(12) United States Patent
Labelle et al.

(10) Patent No.: US 6,410,583 B1
(45) Date of Patent: Jun. 25, 2002

(54) CYCLOPENTANOINDOLES, COMPOSITIONS CONTAINING SUCH COMPOUNDS AND METHODS OF TREATMENT

(75) Inventors: Marc Labelle, Burlingame, CA (US); Claudio Sturino, Dorval (CA); Bruno Roy, Ile Bizard (CA); Carl Berthelette, Ste-Dorothee Laval (CA); Michael Boyd, Montreal (CA); Nicolas Lachance, Pierrefonds (CA); John Scheigetz, Dollard des Ormeaux (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/909,636

(22) Filed: Jul. 20, 2001

Related U.S. Application Data

(60) Provisional application No. 60/220,683, filed on Jul. 25, 2000.

(51) Int. Cl.[7] ..................... A61K 31/403; C07D 209/58
(52) U.S. Cl. ..................... 514/411; 548/439; 548/448
(58) Field of Search .......................... 514/411; 548/439, 548/448

(56) References Cited

U.S. PATENT DOCUMENTS

| | | | |
|---|---|---|---|
| 3,535,326 A | * 10/1970 | Yamamoto et al. ........... 546/86 |
| 3,862,953 A | 1/1975 | Berger et al. | |
| 4,009,181 A | 2/1977 | Berger et al. | |
| 4,057,559 A | 11/1977 | Asselin et al. | |
| 4,808,608 A | 2/1989 | Guindon et al. | |

FOREIGN PATENT DOCUMENTS

| | | |
|---|---|---|
| EP | 0234 708 | 9/1987 |
| EP | 0300 676 | 1/1989 |
| EP | 0468 785 A2 | 1/1992 |
| EP | 0 496 237 | 7/1992 |

OTHER PUBLICATIONS

Cheng et al., Chemical Abstracts, 120:270933, 1994.*

Raucher, et al., Tetrahedron Letters, vol. 39, pp. 3731–3735, 1983.

Kerr, et al., Tetrahedron Letters, vol. 40, pp. 5671–5675, 1999.

09/817,987 Labelle, et al. Feb. 1989.

* cited by examiner

Primary Examiner—Fiona T. Powers
(74) Attorney, Agent, or Firm—Mollie M. Yang; David L. Rose

(57) ABSTRACT

Substituted cyclopentanoindole derivatives are antagonists of prostaglandins, and as such are useful for the treatment of prostaglandin mediated diseases.

15 Claims, No Drawings

CYCLOPENTANOINDOLES, COMPOSITIONS CONTAINING SUCH COMPOUNDS AND METHODS OF TREATMENT

This application claims priority under U.S. provisioal application 60/220,683 filed on Jul. 25, 2000, which is hereby incoporated by reference in its entirety.

BACKGROUND OF THE INVENTION

The present invention relates to compounds and methods for treating prostaglandin mediated diseases, and certain pharmaceutical compositions thereof. More particularly, the compounds of the invention are structurally different from steroids, antihistamines or adreneigic agonists, and are antagonists of the nasal and pulmonary congestion effects of D-type prostaglandins.

Two review articles describe the characterization and therapeutic relevance of the prostanoid receptors as well as the most commonly used selective agonists and antagonists: *Eicosanoids: From Biotechnology to Therapeutic Applications,* Folco, Samucisson, Maclouf, and Velo eds, Plenum Press, New York, 1996, chap. 14, 137–154 and Journal of Lipid Mediators and Cell Signalling, 1996, 14, 83–87. An article from T. Tsuri et al. published in 1997 in Journal of Medicinal Chemistry, vol 40, pp.3504–3507 states that "PGD2 is considered to be an important mediator in various allergic diseases such allergic rhinitis, atopic asthma, allergic conjunctivitis and atopic dermatitis." More recently, an article by Matsuoka et al. in *Science* (2000), 287:2013–7, describes PGD2 as being a key mediator in allergic asthma. In addition, patents such as U.S. Pat. No. 4,808,608 refer to prostaglandin antagonists as useful in the treatment of allergic diseases, and explicitly allergic asthma. PGD2 antagonists are described in, for example, European Patent Application 837,052 and PCT Application WO98/25919, as well as WO99/62555.

U.S. Pat. No. 4,808,608 discloses tetrahydrocarbazole-1-alkanoic acid derivatives as prostaglandin antagonists.

European Patent Application 468,785 discloses the compound 4-[(4-chlorophenyl)methyl]-1,2,3,4-tetrahydro-7-(2-quinolinylmethoxy)-cyclopent[b]indole-3-acetic acid, which is a species of a genus said to be leukotriene biosynthesis inhibitors.

U.S. Pat. No. 3,535,326 discloses antiphlogistic compounds of the formula:

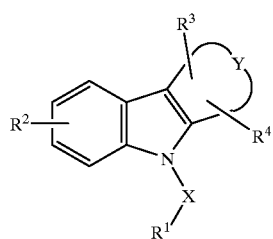

SUMMARY OF THE INVENTION

The present invention provides novel compounds which are prostaglandin receptor antagonists, more particularly, they are prostaglandin D2 receptor (DP receptor) antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

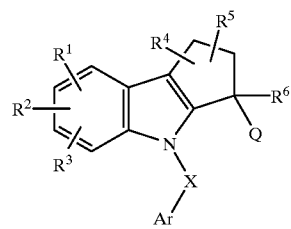

and pharmaceutically acceptable salts, hydrates and esters thereof, wherein:

$R^1$, $R^2$ and $R^3$ are each independently selected from the group consisting of:
(1) hydrogen, and
(2) $R^c$, $R^4$ and $R^5$ are each independently selected from the group consisting of:
(1) H,
(2) F,
(3) CN,
(4) $C_{1-6}$alkyl,
(5) $OR^a$, and
(6) $S(O)_nC_{1-6}$alkyl,
wherein each of said alkyl group is optionally substituted with halogen, or $R^4$ and $R^5$ on the same carbon atom may represent an oxo, or $R^4$ and $R^5$ on the same carbon atom or on adjacent carbon atoms taken together form a 3- or 4-membered ring containing 0 or 1 heteroatom selected from N, S, or O optionally substituted with one or two groups selected from F, $CF_3$ and $CH_3$;

$R^6$ is selected from the group consisting of:
(1) H,
(2) $C_{1-6}$alkyl optionally substituted with one to six groups independently selected from $OR^a$ and halogen, and
(3) heterocyclyl optionally substituted with one to four halogen; or $R^5$ and $R^6$ attached on adjacent carbon atoms together form a 3- or 4-membered ring containing 0 or 1 heteroatom selected from N, S, or O optionally substituted with one or two groups selected from F, $CF_3$ and $CH_3$;

X is selected from the group consisting of: C=O, $SO_2$, and $C_{1-4}$alkyl wherein said alkyl is optionally substituted with one to six halogen;

Ar is aryl or heteroaryl each optionally substituted with one to four groups independently selected from $R^c$;

Q is $C_{1-6}$alkyl optionally substituted with one to six groups independently selected from:
(1) halogen,
(2) aryl,
(3) heteroaryl,
(4) OH, (5) OC$_{1-6}$alkyl,
(6) COOH,
(7) CONR$^a$R$^b$,
(8) C(O)NSO$_2$R$^7$,
(9) tetrazolyl,
wherein aryl, heteroaryl and alkyl are each optionally substituted with one to six groups independently selected from halogen, CF$_3$, and COOH; or Q and R$^6$ together form a 3- or 4-membered ring optionally containing a heteroatom selected from N, S, and O, and optionally substituted with one or two groups independently selected from:
(1) halogen,
(2) oxo,
(3) OR$^a$,
(4) COOH,
(5) C(O)NHSO$_2$R$^7$, and
(6) tetrazolyl, R$^7$ is selected from the group consisting of:
(1) C$_{1-6}$alkyl optionally substituted with one to six halogen,
(2) aryl, and
(3) heteroaryl,
wherein said aryl and heteroaryl are optionally substituted with halogen, OC$_{1-5}$alkyl, C$_{1-5}$alkyl and wherein said alkyl is optionally substituted with one to six halogen;

R$^a$ and R$^b$ are independently selected from hydrogen and C$_{1-6}$alkyl optionally substituted with one to six halogen;

R$^c$ is
(1) halogen,
(2) CN,
(3) C$_{1-6}$alkyl optionally substituted with one to six groups independently selected from halogen, NR$^a$R$^b$, C(O)R$^a$, C(OR$^a$)R$^a$R$^b$, and OR$^a$,
(4) C$_{2-6}$alkenyl optionally substituted with one to six groups independently selected from halogen and OR$^a$,
(5) heterocyclyl,
(6) aryl,
(7) heteroaryl,
(8) C(O)R$^a$,
(9) C(OR$^a$)R$^a$R$^b$,
(10) C(O)OR$^a$,
(11) CONR$^a$R$^b$,
(12) OCONR$^a$R$^b$,
(13) S(O)$_n$R$^7$,
(14) NR$^a$C(O)OC$_{1-6}$alkyl, wherein alkyl is optionally substituted with one to six halogen, and
(15) S(O)$_n$NR$^a$R$^b$,
wherein heterocyclyl, aryl, heteroaryl are optionally substituted with one to four groups independently selected from halogen;

n is 0, 1 or 2.

The invention also encompasses pharmaceutical compositions containing a compound of formula I, and methods for treatment or prevention of prostaglandin mediated diseases using compounds of formula I.

The numbering of the core tricyclic ring system is as shown below:

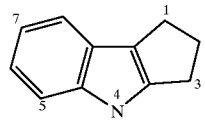

The invention is described using the following definitions unless otherwise indicated.

The term "halogen" or "halo" includes F, Cl, Br, and I.

The term "alkyl" refers to linear, branched and cyclic and bicyclic structures and combinations thereof, containing the indicated number of atoms. Non-limiting examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclobutyl, cyclopentyl, cyclohexyl, cycloheptyl, cyclopropylmethyl, cyclopentylethyl, methyl substituted cyclopropyl, ethyl substituted cyclobutyl, adamantyl, cyclododecylmethyl, 2-ethyl-1-bicyclo[4.4.0]decyl and the like. The term C$_{1-6}$alkyl encompasses acyclic alkyl groups having the indicated number of carbon atoms as well as —C$_x$alkyl-C$_z$cycloalkyl wherein x is 0 to 3 and z is 3 to 6 with the proviso that x+z=3 to 6.

"Haloalkyl" means an alkyl group as described above wherein one or more hydrogen atoms have been replaced by halogen atoms, with up to complete substitution of all hydrogen atoms with halo groups. C$_{1-6}$haloalkyl, for example, includes —CF$_3$, —CF$_2$CF$_3$ and the like.

"Alkoxy" means alkoxy groups of a straight, branched or cyclic configuration having the indicated number of carbon atoms. C$_{1-6}$alkoxy, for example, includes methoxy, ethoxy, propoxy, isopropoxy, and the like.

"Haloalkoxy" means an alkoxy group as described above in which one or more hydrogen atoms have been replaced by halogen atoms, with up to complete substitution of all hydrogen atoms with halo groups. C$_{1-6}$haloalkoxy, for example, includes —OCF$_3$, —OCF$_2$CF$_3$ and the like.

"Alkenyl" means linear or branched structures and combinations thereof, of the indicated number of carbon atoms, having at least one carbon-to-carbon double bond, wherein hydrogen may be replaced by an additional carbon-to-carbon double bond. C$_{2-6}$alkenyl, for example, includes ethenyl, propenyl, 1-methyl-ethenyl, butenyl and the like.

"Heterocyclyl" refers to a non-aromatic ring having 1 to 4 heteroatoms said ring being isolated or fused to a second ring selected from 3- to 7-membered alicyclic ring containing 0 to 4 heteroatoms, aryl and heteroaryl, wherein said heteroatoms are independently selected from O, N and S. Non-limiting examples of heterocyclyl include oxetanyl, 1,3-dithiacyclopentane, dihydrobenzofuran, and the like.

"Aryl" means a 6–14 membered carbocyclic aromatic ring system comprising 1–3 benzene rings. If two or more aromatic rings are present, then the rings are fused together, so that adjacent rings share a common bond. Examples include phenyl and naphthyl.

The term "heteroaryl" (Het) as used herein represents a 5–10 membered aromatic ring system containing one ring or two fused rings, 1–4 heteroatoms, selected from O, S and N. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine.

For purposes of this specification, the following abbreviations have the indicated meanings:

BOC=t-butyloxycarbonyl
CBZ=carbobenzoxy
DCC=1,3-dicyclohexylcarbodiimide
DIBAL=diisobutyl aluminum hydride
DIEA=N,N-diisoproylethylamine
DMAP=4-(dimethylamino)pyridine
DMF=dimethylformamide
EDCI=1-(3-dimethylaminopropyl)-3-ethylcarbodiimide hydrochloride
EDTA=ethylenediaminetetraacetic acid, tetrasodium salt hydrate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOBt=1-hydroxybenzotriazole
HRMS=high resolution mass spectrometry
ICBF=isobutyl chloroformate
KHMDS=potassium hexamethyldisilazane
LDA=lithium diisopropylamide
MCPBA=metachloroperbenzoic acid
Ms=methanesulfonyl=mesyl
MsO=methanefulfonate=mesylate
NBS=N-bromosuccinimide
NMM=4-methylmorpholine
PCC=pyridinium chlorochromate
PDC=pyridinium dichromate
Ph=phenyl
PPTS=pyridinium p-toluene sulfonate
pTSA=p-toluene sulfonic acid
r.t.=room temperature
rac.=racemic
TfO=trifluoromethanesulfonate=triflate
TLC=thin layer chromatography Alkyl group abbreviations
Me=methyl
Et=ethyl
n-Pr=normal protpyl
i-Pr=isopropyl
c-Pr=cycloprpyl
n-Bu=normal butyl
i-Bu=isobutyl
c-Bu=cyclobutyl
s-Bu=secondary butyl
t-Bu=tertiary butyl In one embodiment of formula I are compounds wherein X is $C_{1-4}$alkyl; more particularly wherein X is $CH_2$.

In another embodiment of formula I are compounds wherein Q is $C_{1-6}$alkyl substituted with COOH or tetrazolyl.

In another embodiment of formula I are compounds wherein Q is $C_{1-3}$alkyl optionally substituted with one to six groups selected from the group consisting of halogen, COOH, tetrazolyl and $CONR^aR^b$ wherein $R^a$ and $R^b$ are independently selected from hydrogen and $C_{1-6}$alkyl optionally substituted with one to six halogen (preferably fluorine). More particularly, Q is $C_{1-3}$alkyl substituted with COOH.

In another embodiment of formula I are compounds wherein Q and $R^6$ together form a 3- or 4-membered ling containing 0 or 1 heteroatom selected from N, S and O, and optionally substituted with one or two groups selected from halogen, OH, COOH, oxo, tetrazolyl, $C(O)NSO_2R^7$, $OC_{1-6}$alkyl wherein said alkyl group is optionally substituted with one to six halogen. More particularly, Q and $R^6$ together form a 3- or 4-membered ring containing 0 or 1 heteroatom selected from N, S and O, and optionally substituted with COOH or tetrazolyl.

In another embodiment of formula I are compounds wherein $R^3$ is H, $R^1$ and $R^2$ are selected from the group consisting of hydrogen, halogen, $C_{1-3}$alkyl (optionally substituted with one to six groups independently selected from halogen, $C(O)R^a$, and $C(OR^a)R^aR^b$), aryl, heteroaryl, heterocyclyl, $C(O)OC_{1-3}$alkyl, $S(O)_nC_{1-3}$alkyl, $S(O)_nNR^aR^b$, $C(O)R^a$, $C(OH)R^aR^b$, and $C(OC_{1-3}alkyl)R^aR^b$, wherein each of aryl, heteroaryl, heterocyclyl, and alkyl is optionally substituted with one to six halogen atoms; n=0, 1 or 2; $R^a$ and $R^b$ are independently selected from hydrogen and $C_{1-6}$alkyl optionally substituted with halogen. Halogen, as used in this embodiment, is preferably fluorine.

In another embodiment of formula I are compounds wherein $R^4$ and $R^5$ are each independently selected from the group consisting of H, $C_{1-4}$alkyl optionally substituted with one to six halogen atoms, preferably fluorine, and $OR^a$ wherein $R^a$ is as defined under formula I, preferably hydrogen; or $R^4$ and $R^5$ attached to the same carbon atom represent an oxo.

In another embodiment of formula I are compounds wherein Ar is aryl or heteroaryl each optionally substituted with one to four groups independently selected from halogen, CN, $C_{1-4}$alkyl optionally substituted with one to six halogen atoms, preferably fluorine, $C(O)R^a$ and $C(OH)R^aR^b$ wherein $R^a$ and $R^b$ are independently selected from hydrogen and $C_{1-6}$alkyl optionally substituted with halogen, preferably fluorine.

In a preferred embodiment of formula I are compounds of formula Ia:

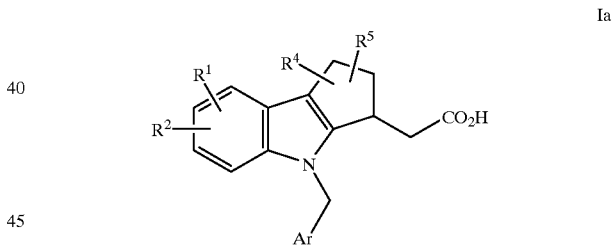

Ia where Ar and $R^1$–$R^4$ are as defined under formula I. In a more preferred embodiment, $R^4$ and $R^5$ are each hydrogen, and $R^1$ represents a non-H substituent at the 7-position.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, moipholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaic, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I are meant to also include the pharmaceutically acceptable salts.

Utilities

The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be use in the treatment of dysmenorrhea, premature labor and eosinophil related disorders. More particularly compounds of formula I are antagonists of prostaglandin D2.

Accordingly, another aspect of the invention provides a method of treating or preventing a prostaglandin mediated disease comprising administering to a mammalian patient in need of such treatment a compound of formula I in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease is to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congenstion, rhinitis incuding allergic and perennial rhintis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, particularly allergic asthma, in a patient in need of such treatment which comprises administering to said patient a therapeutically effective amount of a compound of formula I.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occuring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a prostaglandin D2 antagonist such as S-5751; (2) a corticosteroid such as triamcinolone acetonide; (3) a β-agonist such as salmeterol, formoterol, terbutaline, metaproterenol, albuterol and the like; (4) a leukotriene modifier, including a leukotriene antagonist or a lipooxygenase inhibitor such as montelukast, zafirlukast, pranlukast, or zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, norastemizole, terfenadine, loratadine, cetirizine, levocetirizine, fexofenadine, descarboethoxyloratadine, and the like; (6) a decongestant including phenylephrine, phenylpropanolamine, pseudophedrine, oxymetazoline, ephinephrine. naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazonc, bezpiperylon, feprazone, mofebutazone, oxyphenbutazone, phenylbutazone); (11) cyclooxygenase-2 (COX-2) inhibitors such as celecoxib and rofecoxib, etoricoxib and valdecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidasc inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of the compound of formula I, optionally co-administered with one or more of such ingredients as listed immediately above. The amounts of active ingredients may be those commonly used for each active ingredient when it is administered alone, or in some instances the combination of active ingredients may result in lower dosage for one or more of the active ingredients.

Methods of Synthesis

Compounds of Formula I of the present invention can be prepared according to the synthetic routes outlined in Schemes 1 to 6 and by following the methods described herein.

Intermediate compounds of Formula IV may be prepared by the method presented in Scheme 1 from an appropriately substituted phenyl hydrazine (II). Reaction of II with an appropriate cyclopentanone III under Fisher Indole or similar conditions gives IV.

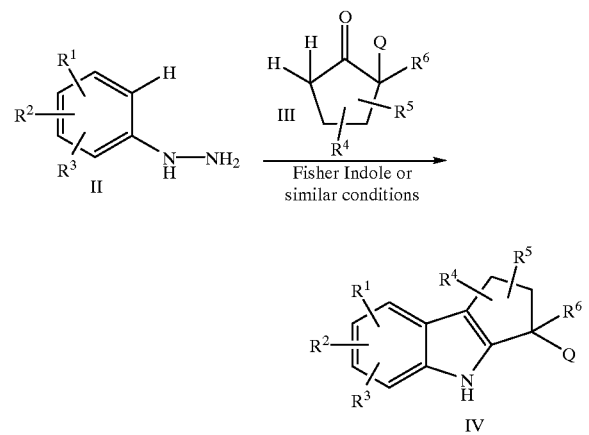

Scheme 1

Compounds of Formula IV may alternatively be prepared by the method presented in Scheme 2 from an appropriately substituted aniline (V). Reaction of V with iodine yields VI. Condensation with an appropriate cyclopentanone III followed by the cyclization under Heck or similar metal catalysis conditions leads to indole IV.

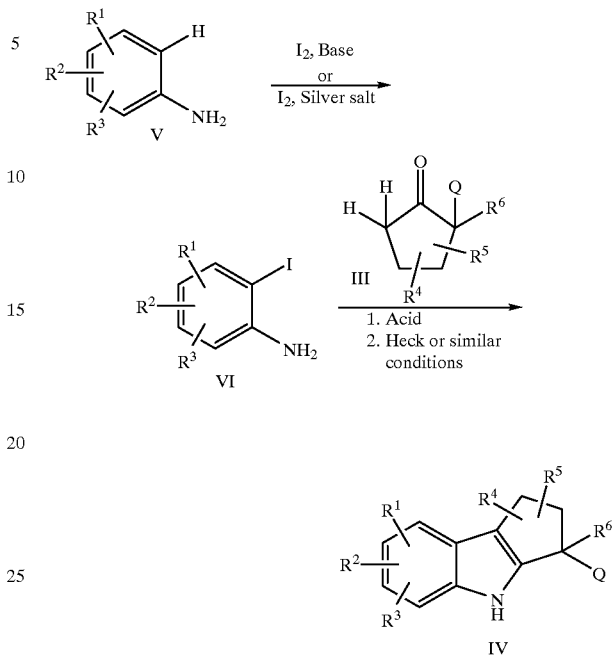

Scheme 2

Compounds of Formula III may be prepared by the method presented in Scheme 3 from an appropriately substituted silyl enol ether (VII) or an appropriately substituted enamine (VIII). Addition of an appropriate electrophile such as QY (wherein Y represents a halogen or a leaving group) in the presence of a base such as an alkyl lithium or a Lewis acid such as silver trifluoroacetate with the silyl enol ether VII gives the cyclopentanone III. The compound of formula III may alternatively be prepared from the addition of QY on an appropriately substituted enamine VIII under Stork Enamine or similar conditions.

Scheme 3

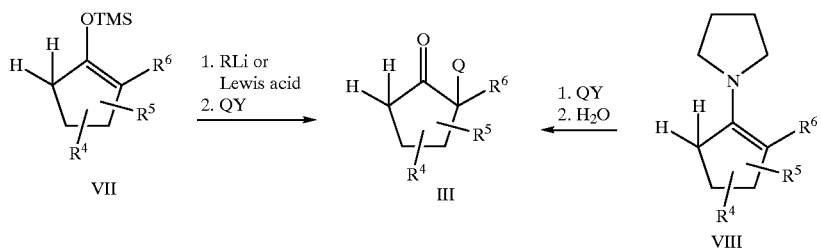

Intermediate compounds of Formula X may be prepared by the method presented in Scheme 4 from an appropriately substituted indole (IX). Bromination of IX may be accomplished with bromine in a polar and basic solvent such as pyridine followed by the mono reduction of a dibromo intermediate under acid and reducing metal conditions to generate the indole X.

Scheme 4

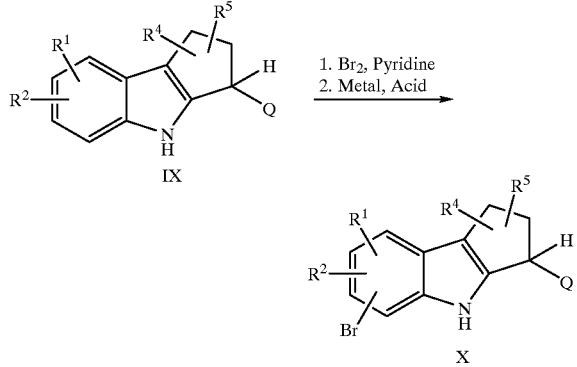

Compounds of Formula I may be prepared by the method presented in Scheme 5 from an appropriately substituted indole (IV). Alkylation of IV with the appropriate electrophile such as ArXY (wherein Y represents a halogen or a leaving group) in the presence of a base and in a suitable solvent such as DMF gives I.

Scheme 5

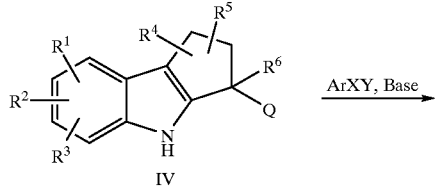

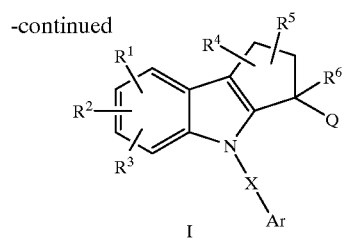

Compounds of Formula I may alternatively be prepared by the method presented in Scheme 6 from an appropriately substituted bromoindole (XI) from compound of formula X following the coupling reaction described in Scheme 5. Palladium coupling or similar reactions of bromoindole XI with an appropriate organometallic compound $R^3M$ (wherein M represents a metal such as B, Mg, Zn or Sn) leads to compound I. The same bromoindole XI may alternatively first react with a suitable metallation agent, such as n-BuLi, followed by trapping with an electrophile such as $R^3Y$ to give compound I.

Scheme 6

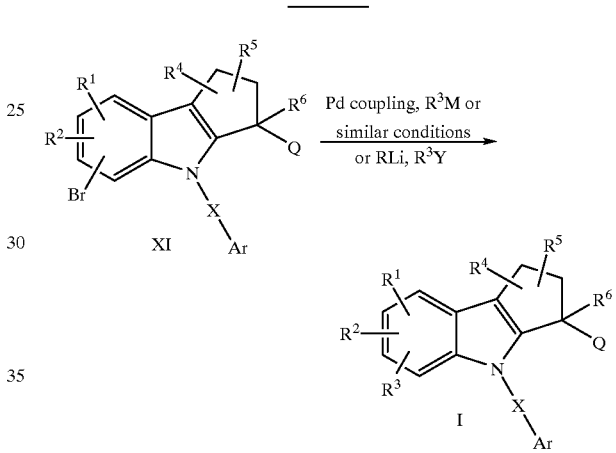

Representative Compounds

Representative compounds of formula I are shown in the following Tables, the substituents are as indicated, and H is meant where no value appears for a particular variable. Each entry is intended to include the racemic or diastereomeric mixture, and the individual enantiomers and/or diastereomers. Methods for the resolution of enantiomers and for the separation of diastereomers are well known to those skilled in the art; selective illustration of such methods are also described in the Examples hereinbelow.

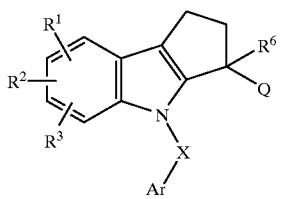

| $R^1/R^2$ | $R^3$ | $Q/R^6$ | X | Ar |
|---|---|---|---|---|
| 7-SO$_2$Me | 5-C(O)CH$_3$ | CH$_2$CO$_2$H | CH$_2$ | 4-Cl-phe |
| 7-SO$_2$Me | 5-CH(OH)CH$_3$ | CH$_2$CO$_2$H | CH$_2$ | 4-Cl-phe |
| 7-SO$_2$Me | 5-Br | CH$_2$CO$_2$H | CH$_2$ | 2,4-Cl$_2$-phe |
| 7-SO$_2$Me | 5-CH=CH$_2$ | CH$_2$CO$_2$H | CH$_2$ | 4-Cl-phe |
| 7-SO$_2$Me | 5-c-pr | CH$_2$CO$_2$H | CH$_2$ | 4-Cl-phe |
| 7-SO$_2$Me | 5-(thiophen-2-yl) | CH$_2$CO$_2$H | CH$_2$ | 4-Cl-phe |

-continued

| | | | | |
|---|---|---|---|---|
| 7-SO$_2$NMe$_2$ | | CH$_2$CO$_2$H | CH$_2$ | 4-Cl-phe |
| 7-F | 5-Br | CH$_2$CO$_2$H/CH$_3$ | CH$_2$ | 4-Cl-phe |
| 5-Br | | CH$_2$CO$_2$H | CH$_2$ | 4-Cl-phe |
| | | CH$_2$CO$_2$H | SO$_2$ | 2,4-Cl$_2$-phe |
| | | CH$_2$CO$_2$H | SO$_2$ | 3,4-Cl$_2$-phe |
| | | CH$_2$CO$_2$H | SO$_2$ | 4-Cl-phe |
| 7-F | | CH$_2$CO$_2$H | CO | 2,4-Cl$_2$-phe |
| 7-F | | CH$_2$CO$_2$H | CO | 3,4-Cl$_2$-phe |
| 7-F | | CH$_2$CO$_2$H | CO | 4-Cl-phe |
| 7-CF$_3$ | | CH$_2$CO$_2$H | CH$_2$ | 2,4-Cl$_2$-phe |
| 7-CF$_3$ | | CH$_2$CO$_2$H | CH$_2$ | 3,4-Cl$_2$-phe |
| 7-CF$_3$ | | CH$_2$CO$_2$H | CHCH$_3$ | 3,4-Cl$_2$-phe |
| 7-CF$_3$ | | CH$_2$CO$_2$H | CH$_2$ | 4-Cl-phe |
| 7-F | | CH(CH$_3$)CO$_2$H | CH$_2$ | 2,4-Cl$_2$-phe |
| 7-F | | CH$_2$CO$_2$H | CH$_2$ | 2,4-Cl$_2$-phe |
| 7-F | | CH$_2$CO$_2$H | CH$_2$ | 3,4-Cl$_2$-phe |
| 7-F | | CH$_2$CO$_2$H | CH$_2$ | 4-Cl-phe |
| 7-F | | CH$_2$CO$_2$H | CH$_2$ | 2-Cl-4-F-phe |
| 7-F | | CH$_2$CO$_2$H | CH$_2$ | 2-F-4-Cl-phe |
| 7-F | | CH$_2$CO$_2$H | 1,1-cPr | 4-Cl-phe |
| 7-F | | CH$_2$CO$_2$H | CH$_2$ | 2,4,6-Cl$_3$-phe |
| 7-F | | CH$_2$CO$_2$H | CH$_2$ | 2,3,4-Cl$_3$-phe |
| 7-F | | CH$_2$CO$_2$H | CH$_2$ | 2-Br-4-Cl-phe |
| 7-F | | CH$_2$CO$_2$H | CH$_2$ | 2-Cl-4-Br-phe |
| 7-F | | CH$_2$CO$_2$H | CH$_2$ | 2-F-4-Br-phe |
| 7-F | | CH$_2$CO$_2$H | CH$_2$ | 2-Cl-4-CN-phe |
| 7-F | | CH$_2$CO$_2$H | CH$_2$ | 2-Cl-4-COCH$_3$-phe |
| 7-F | | CH$_2$CO$_2$H | CH$_2$ | 4-CN-phe |
| 7-F | | CH$_2$CO$_2$H | CH$_2$ | 4-COCH$_3$-phe |
| 7-F | | CH$_2$CO$_2$H | CH$_2$ | 3-Cl-4-CN-phe |
| 7-F | | CH$_2$CO$_2$H | CH$_2$ | 3-Cl-4-COCH$_3$-phe |
| 7-F | | CH$_2$CO$_2$H | CH$_2$ | 4-CF$_3$-phe |
| 7-F | | CH$_2$CO$_2$H | CH$_2$ | 2-Cl-4-CF$_3$-phe |
| 7-F | | CH$_2$CO$_2$H | CH$_2$ | 3-Cl-4-CF$_3$-phe |
| 7-F | | CH$_2$CO$_2$H | CH$_2$ | 2,6-Cl$_2$-phe |
| 7-F | | CH$_2$CO$_2$H | CH$_2$ | 2,4,6-F$_3$-phe |
| 7-F | 5-CO$_2$Me | CH(CH$_3$)CO$_2$H | CH$_2$ | 2,4-Cl$_2$-phe |
| 7-F | 5-CO$_2$Me | CH$_2$CO$_2$H | CH$_2$ | 2,4-Cl$_2$-phe |
| 7-F | 5-CO$_2$Me | CH$_2$CO$_2$H | CH$_2$ | 3,4-Cl$_2$-phe |
| 7-F | 5-CO$_2$Me | CH$_2$CO$_2$H | CH$_2$ | 4-Cl-phe |
| 7-F | 5-CO$_2$Me | CH$_2$CO$_2$H | CH$_2$ | 2-Cl-4-F-phe |
| 7-F | 5-CO$_2$Me | CH$_2$CO$_2$H | CH$_2$ | 2-F-4-Cl-phe |
| 7-F | 5-CO$_2$Me | CH$_2$CO$_2$H | 1,1-c-pr | 4-Cl-phe |
| 7-F | 5-CO$_2$Me | CH$_2$CO$_2$H | CH$_2$ | 2,4,6-Cl$_3$-phe |
| 7-F | 5-CO$_2$Me | CH$_2$CO$_2$H | CH$_2$ | 2,3,4-Cl$_3$-phe |
| 7-F | 5-CO$_2$Me | CH$_2$CO$_2$H | CH$_2$ | 2-Br-4-Cl-phe |
| 7-F | 5-CO$_2$Me | CH$_2$CO$_2$H | CH$_2$ | 2-Cl-4-Br-phe |
| 7-F | 5-CO$_2$Me | CH$_2$CO$_2$H | CH$_2$ | 2-F-4-Br-phe |
| 7-F | 5-CO$_2$Me | CH$_2$CO$_2$H | CH$_2$ | 2-Cl-4-CN-phe |
| 7-F | 5-CO$_2$Me | CH$_2$CO$_2$H | CH$_2$ | 2-Cl-4-COCH$_3$-phe |
| 7-F | 5-CO$_2$Me | CH$_2$CO$_2$H | CH$_2$ | 4-CN-phe |
| 7-F | 5-CO$_2$Me | CH$_2$CO$_2$H | CH$_2$ | 4-COCH$_3$-phe |
| 7-F | 5-CO$_2$Me | CH$_2$CO$_2$H | CH$_2$ | 3-Cl-4-CN-phe |
| 7-F | 5-CO$_2$Me | CH$_2$CO$_2$H | CH$_2$ | 3-Cl-4-COCH$_3$-phe |
| 7-F | 5-CO$_2$Me | CH$_2$CO$_2$H | CH$_2$ | 4-CF$_3$-phe |
| 7-F | 5-CO$_2$Me | CH$_2$CO$_2$H | CH$_2$ | 2-Cl-4-CF$_3$-phe |
| 7-F | 5-CO$_2$Me | CH$_2$CO$_2$H | CH$_2$ | 3-Cl-4-CF$_3$-phe |
| 7-F | 5-CO$_2$Me | CH$_2$CO$_2$H | CH$_2$ | 2,6-Cl$_2$-phe |
| 7-F | 5-CO$_2$Me | CH$_2$CO$_2$H | CH$_2$ | 2,4,6-F$_3$-phe |
| 7-F | 5-SOMe | CH(CH$_3$)CO$_2$H | CH$_2$ | 2,4-Cl$_2$-phe |
| 7-F | 5-SOMe | CH$_2$CO$_2$H | CH$_2$ | 2,4-Cl$_2$-phe |
| 7-F | 5-SOMe | CH$_2$CO$_2$H | CH$_2$ | 3,4-Cl$_2$-phe |
| 7-F | 5-SOMe | CH$_2$CO$_2$H | CH$_2$ | 4-Cl-phe |
| 7-F | 5-SOMe | CH$_2$CO$_2$H | CH$_2$ | 2-Cl-4-F-phe |
| 7-F | 5-SOMe | CH$_2$CO$_2$H | CH$_2$ | 2-F-4-Cl-phe |
| 7-F | 5-SOMe | CH$_2$CO$_2$H | 1,1-c-pr | 4-Cl-phe |
| 7-F | 5-SOMe | CH$_2$CO$_2$H | CH$_2$ | 2,4,6-Cl$_3$-phe |
| 7-F | 5-SOMe | CH$_2$CO$_2$H | CH$_2$ | 2,3,4-Cl$_3$-phe |
| 7-F | 5-SOMe | CH$_2$CO$_2$H | CH$_2$ | 2-Br-4-Cl-phe |
| 7-F | 5-SOMe | CH$_2$CO$_2$H | CH$_2$ | 2-Cl-4-Br-phe |
| 7-F | 5-SOMe | CH$_2$CO$_2$H | CH$_2$ | 2-F-4-Br-phe |
| 7-F | 5-SOMe | CH$_2$CO$_2$H | CH$_2$ | 2-Cl-4-CN-phe |
| 7-F | 5-SOMe | CH$_2$CO$_2$H | CH$_2$ | 2-Cl-4-COCH$_3$-phe |
| 6,7-F$_2$ | 5-SOMe | CH$_2$CO$_2$H | CH$_2$ | 4-CN-phe |
| 7-F | 5-SOMe | CH$_2$CO$_2$H | CH$_2$ | 4-COCH$_3$-phe |
| 7-F | 5-SOMe | CH$_2$CO$_2$H | CH$_2$ | 3-Cl-4-CN-phe |
| 7-F | 5-SOMe | CH$_2$CO$_2$H | CH$_2$ | 3-Cl-4-COCH$_3$-phe |
| 7-F | 5-SOMe | CH$_2$CO$_2$H | CH$_2$ | 4-CF$_3$-phe |
| 7-F | 5-SOMe | CH$_2$CO$_2$H | CH$_2$ | 2-Cl-4-CF$_3$-phe |

-continued

| | | | | |
|---|---|---|---|---|
| 7-F | 5-SOMe | CH$_2$CO$_2$H | CH$_2$ | 3-Cl-4-CF$_3$-phe |
| 7-F | 5-SOMe | CH$_2$CO$_2$H | CH$_2$ | 2,6-Cl$_2$-phe |
| 7-F | 5-SOMe | CH$_2$CO$_2$H | CH$_2$ | 2,4,6-F$_3$-phe |
| 7-SO$_2$Me | 5-C(O)CH$_3$ | CH(CH$_3$)CO$_2$H | CH$_2$ | 2,4-Cl$_2$-phe |
| 7-SO$_2$Me | 5-C(O)CH$_3$ | CH$_2$CO$_2$H | CH$_2$ | 2,4-Cl$_2$-phe |
| 7-SO$_2$Me | 5-C(O)CH$_3$ | CH$_2$CO$_2$H | CH$_2$ | 3,4-Cl$_2$-phe |
| 7-SO$_2$Me | 5-C(O)CH$_3$ | CH$_2$CO$_2$H | CH$_2$ | 2-Cl-4-F-phe |
| 7-SO$_2$Me | 5-C(O)CH$_3$ | CH$_2$CO$_2$H | CH$_2$ | 2-F-4-Cl-phe |
| 7-SO$_2$Me | 5-C(O)CH$_3$ | CH$_2$CO$_2$H | 1,1-c-pr | 4-Cl-phe |
| 7-SO$_2$Me | 5-C(O)CH$_3$ | CH$_2$CO$_2$H | CH$_2$ | 2,4,6-Cl$_3$-phe |
| 7-SO$_2$Me | 5-C(O)CH$_3$ | CH$_2$CO$_2$H | CH$_2$ | 2,3,4-Cl$_3$-phe |
| 7-SO$_2$Me | 5-C(O)CH$_3$ | CH$_2$CO$_2$H | CH$_2$ | 2-Br-4-Cl-phe |
| 7-SO$_2$Me | 5-C(O)CH$_3$ | CH$_2$CO$_2$H | CH$_2$ | 2-Cl-4-Br-phe |
| 7-SO$_2$Me | 5-C(O)CH$_3$ | CH$_2$CO$_2$H | CH$_2$ | 2-F-4-Br-phe |
| 7-SO$_2$Me | 5-C(O)CH$_3$ | CH$_2$CO$_2$H | CH$_2$ | 2-Cl-4-CN-phe |
| 7-SO$_2$Me | 5-C(O)CH$_3$ | CH$_2$CO$_2$H | CH$_2$ | 2-Cl-4-COCH$_3$-phe |
| 7-SO$_2$Me | 5-C(O)CH$_3$ | CH$_2$CO$_2$H | CH$_2$ | 4-CN-phe |
| 7-SO$_2$Me | 5-C(O)CH$_3$ | CH$_2$CO$_2$H | CH$_2$ | 4-COCH$_3$-phe |
| 7-SO$_2$Me | 5-C(O)CH$_3$ | CH$_2$CO$_2$H | CH$_2$ | 3-Cl-4-CN-phe |
| 7-SO$_2$Me | 5-C(O)CH$_3$ | CH$_2$CO$_2$H | CH$_2$ | 3-Cl-4-COCH$_3$-phe |
| 7-SO$_2$Me | 5-C(O)CH$_3$ | CH$_2$CO$_2$H | CH$_2$ | 4-CF$_3$-phe |
| 7-SO$_2$Me | 5-C(O)CH$_3$ | CH$_2$CO$_2$H | CH$_2$ | 2-Cl-4-CF$_3$-phe |
| 7-SO$_2$Me | 5-C(O)CH$_3$ | CH$_2$CO$_2$H | CH$_2$ | 3-Cl-4-CF$_3$-phe |
| 7-SO$_2$Me | 5-C(O)CH$_3$ | CH$_2$CO$_2$H | CH$_2$ | 2,6-Cl$_2$-phe |
| 7-SO$_2$Me | 5-C(O)CH$_3$ | CH$_2$CO$_2$H | CH$_2$ | 2,4,6-F$_3$-phe |
| 7-SO$_2$Me | 5-CH(OH)CH$_3$ | CH(CH$_3$)CO$_2$H | CH$_2$ | 2,4-Cl$_2$-phe |
| 7-SO$_2$Me | 5-CH(OH)CH$_3$ | CH$_2$CO$_2$H | CH$_2$ | 2,4-Cl$_2$-phe |
| 7-SO$_2$Me | 5-CH(OH)CH$_3$ | CH$_2$CO$_2$H | CH$_2$ | 3,4-Cl$_2$-phe |
| 7-SO$_2$Me | 5-CH(OH)CH$_3$ | CH$_2$CO$_2$H | CH$_2$ | 2-Cl-4-F-phe |
| 7-SO$_2$Me | 5-CH(OH)CH$_3$ | CH$_2$CO$_2$H | CH$_2$ | 2-F-4-Cl-phe |
| 7-SO$_2$Me | 5-CH(OH)CH$_3$ | CH$_2$CO$_2$H | 1,1-c-pr | 4-Cl-phe |
| 7-SO$_2$Me | 5-CH(OH)CH$_3$ | CH$_2$CO$_2$H | CH$_2$ | 2,4,6-Cl$_3$-phe |
| 7-SO$_2$Me | 5-CH(OH)CH$_3$ | CH$_2$CO$_2$H | CH$_2$ | 2,3,4-Cl$_3$-phe |
| 7-SO$_2$Me | 5-CH(OH)CH$_3$ | CH$_2$CO$_2$H | CH$_2$ | 2-Br-4-Cl-phe |
| 7-SO$_2$Me | 5-CH(OH)CH$_3$ | CH$_2$CO$_2$H | CH$_2$ | 2-Cl-4-Br-phe |
| 7-SO$_2$Me | 5-CH(OH)CH$_3$ | CH$_2$CO$_2$H | CH$_2$ | 2-F-4-Br-phe |
| 7-SO$_2$Me | 5-CH(OH)CH$_3$ | CH$_2$CO$_2$H | CH$_2$ | 2-Cl-4-CN-phe |
| 7-SO$_2$Me | 5-CH(OH)CH$_3$ | CH$_2$CO$_2$H | CH$_2$ | 2-Cl-4-COCH$_3$-phe |
| 7-SO$_2$Me | 5-CH(OH)CH$_3$ | CH$_2$CO$_2$H | CH$_2$ | 4-CN-phe |
| 7-SO$_2$Me | 5-CH(OH)CH$_3$ | CH$_2$CO$_2$H | CH$_2$ | 4-COCH$_3$-phe |
| 7-SO$_2$Me | 5-CH(OH)CH$_3$ | CH$_2$CO$_2$H | CH$_2$ | 3-Cl-4-CN-phe |
| 7-SO$_2$Me | 5-CH(OH)CH$_3$ | CH$_2$CO$_2$H | CH$_2$ | 3-Cl-4-COCH$_3$-phe |
| 7-SO$_2$Me | 5-CH(OH)CH$_3$ | CH$_2$CO$_2$H | CH$_2$ | 4-CF$_3$-phe |
| 7-SO$_2$Me | 5-CH(OH)CH$_3$ | CH$_2$CO$_2$H | CH$_2$ | 2-Cl-4-CF$_3$-phe |
| 7-SO$_2$Me | 5-CH(OH)CH$_3$ | CH$_2$CO$_2$H | CH$_2$ | 3-Cl-4-CF$_3$-phe |
| 7-SO$_2$Me | 5-CH(OH)CH$_3$ | CH$_2$CO$_2$H | CH$_2$ | 2,6-Cl$_2$-phe |
| 7-SO$_2$Me | 5-CH(OH)CH$_3$ | CH$_2$CO$_2$H | CH$_2$ | 2,4,6-F$_3$-phe |
| 7-SO$_2$Me | 5-CO$_2$CH$_3$ | CH(CH$_3$)CO$_2$H | CH$_2$ | 2,4-Cl$_2$-phe |
| 7-SO$_2$Me | 5-CO$_2$CH$_3$ | CH$_2$CO$_2$H | CH$_2$ | 2,4-Cl$_2$-phe |
| 7-SO$_2$Me | 5-CO$_2$CH$_3$ | CH$_2$CO$_2$H | CH$_2$ | 3,4-Cl$_2$-phe |
| 7-SO$_2$Me | 5-CO$_2$CH$_3$ | CH$_2$CO$_2$H | CH$_2$ | 4-Cl-phe |
| 7-SO$_2$Me | 5-CO$_2$CH$_3$ | CH$_2$CO$_2$H | CH$_2$ | 2-Cl-4-F-phe |
| 7-SO$_2$Me | 5-CO$_2$CH$_3$ | CH$_2$CO$_2$H | CH$_2$ | 2-F-4-Cl-phe |
| 7-SO$_2$Me | 5-CO$_2$CH$_3$ | CH$_2$CO$_2$H | 1,1-c-pr | 4-Cl-phe |
| 7-SO$_2$Me | 5-CO$_2$CH$_3$ | CH$_2$CO$_2$H | CH$_2$ | 2,4,6-Cl$_3$-phe |
| 7-SO$_2$Me | 5-CO$_2$CH$_3$ | CH$_2$CO$_2$H | CH$_2$ | 2,3,4-Cl$_3$-phe |
| 7-SO$_2$Me | 5-CO$_2$CH$_3$ | CH$_2$CO$_2$H | CH$_2$ | 2-Br-4-Cl-phe |
| 7-SO$_2$Me | 5-CO$_2$CH$_3$ | CH$_2$CO$_2$H | CH$_2$ | 2-Cl-4-Br-phe |
| 7-SO$_2$Me | 5-CO$_2$CH$_3$ | CH$_2$CO$_2$H | CH$_2$ | 2-F-4-Br-phe |
| 7-SO$_2$Me | 5-CO$_2$CH$_3$ | CH$_2$CO$_2$H | CH$_2$ | 2-Cl-4-CN-phe |
| 7-SO$_2$Me | 5-CO$_2$CH$_3$ | CH$_2$CO$_2$H | CH$_2$ | 2-Cl-4-COCH$_3$-phe |
| 7-SO$_2$Me | 5-CO$_2$CH$_3$ | CH$_2$CO$_2$H | CH$_2$ | 4-CN-phe |
| 7-SO$_2$Me | 5-CO$_2$CH$_3$ | CH$_2$CO$_2$H | CH$_2$ | 4-COCH$_3$-phe |
| 7-SO$_2$Me | 5-CO$_2$CH$_3$ | CH$_2$CO$_2$H | CH$_2$ | 3-Cl-4-CN-phe |
| 7-SO$_2$Me | 5-CO$_2$CH$_3$ | CH$_2$CO$_2$H | CH$_2$ | 3-Cl-4-COCH$_3$-phe |
| 7-SO$_2$Me | 5-CO$_2$CH$_3$ | CH$_2$CO$_2$H | CH$_2$ | 4-CF$_3$-phe |
| 7-SO$_2$Me | 5-CO$_2$CH$_3$ | CH$_2$CO$_2$H | CH$_2$ | 2-Cl-4-CF$_3$-phe |
| 7-SO$_2$Me | 5-CO$_2$CH$_3$ | CH$_2$CO$_2$H | CH$_2$ | 3-Cl-4-CF$_3$-phe |
| 7-SO$_2$Me | 5-CO$_2$CH$_3$ | CH$_2$CO$_2$H | CH$_2$ | 2,6-Cl$_2$-phe |
| 7-SO$_2$Me | 5-CO$_2$CH$_3$ | CH$_2$CO$_2$H | CH$_2$ | 2,4,6-F$_3$-phe |
| 7-SO$_2$Me | 5-CO$_2$CH$_3$ | CH$_2$CO$_2$H | SO$_2$ | 2,4-Cl$_2$-phe |
| 7-SO$_2$Me | 5-CO$_2$CH$_3$ | CH$_2$CO$_2$H | SO$_2$ | 3,4-Cl$_2$-phe |
| 7-SO$_2$Me | 5-CO$_2$CH$_3$ | CH$_2$CO$_2$H | SO$_2$ | 4-Cl-phe |
| 7-SOMe | 5-CO$_2$CH$_3$ | CH$_2$CO$_2$H | CH$_2$ | 2,4-Cl$_2$-phe |
| 7-SOMe | 5-CO$_2$CH$_3$ | CH$_2$CO$_2$H | CH$_2$ | 3,4-Cl$_2$-phe |
| 7-SOMe | 5-CO$_2$CH$_3$ | CH$_2$CO$_2$H | CH$_2$ | 4-Cl-phe |
| 7-SO$_2$Me | 5-CO$_2$CH$_3$ | CHCH$_3$CO$_2$H | CH$_2$ | 2,4-Cl$_2$-phe |
| 7-SO$_2$Me | 5-CO$_2$CH$_3$ | CHCH$_3$CO$_2$H | CH$_2$ | 3,4-Cl$_2$-phe |
| 7-SO$_2$Me | 5-CO$_2$CH$_3$ | CHCH$_3$CO$_2$H | CH$_2$ | 4-Cl-phe |

-continued

| | | | | |
|---|---|---|---|---|
| 7-SO₂Me | 5-CO₂CH₃ | CH₂CO₂H/CH₃ | CH₂ | 2,4-Cl₂-phe |
| 7-SO₂Me | 5-CO₂CH₃ | CH₂CO₂H/CH₃ | CH₂ | 3,4-Cl₂-phe |
| 7-SO₂Me | 5-CO₂CH₃ | CH₂CO₂H/CH₃ | CH₂ | 4-Cl-phe |
| 7-SO₂Me | 5-CO₂CH₂CH₃ | CH₂CO₂H | CH₂ | 3,4-Cl₂-phe |
| 7-SO₂Me | 5-CO₂CH₂CH₃ | CH₂CO₂H | CH₂ | 4-Cl-phe |
| 7-SO₂Me | 5-C(OH)(CH₂)₂ | CH₂CO₂H | CH₂ | 2,4-Cl₂-phe |
| 7-SO₂Me | 5-C(OH)(CH₂)₂ | CH₂CO₂H | CH₂ | 3,4-Cl₂-phe |
| 7-SO₂Me | 5-C(OH)(CH₂)₂ | CH₂CO₂H | CH₂ | 4-Cl-phe |
| 7-SO₂Me | 5-(thiophen-2-yl) | CH₂CO₂H | CH₂ | 2,4-Cl₂-phe |
| 7-SO₂Me | 5-(thiophen-2-yl) | CH₂CO₂H | CH₂ | 3,4-Cl₂-phe |
| 7-F | 5-(thiophen-2-yl) | CH₂CO₂H | CH₂ | 2,4-Cl₂-phe |
| 7-F | 5-(thiophen-2-yl) | CH₂CO₂H | CH₂ | 3,4-Cl₂-phe |
| 7-F | 5-(thiophen-2-yl) | CH₂CO₂H | CH₂ | 4-Cl-phe |
| 7-F | 5-(2-oxazolyl) | CH₂CO₂H | CH₂ | 2,4-Cl₂-phe |
| 7-F | 5-(2-oxazolyl) | CH₂CO₂H | CH₂ | 3,4-Cl₂-phe |
| 7-F | 5-(2-oxazolyl) | CH₂CO₂H | CH₂ | 4-Cl-phe |
| 7-SO₂Me | 5-(2-oxazolyl) | CH₂CO₂H | CH₂ | 2,4-Cl₂-phe |
| 7-SO₂Me | 5-(2-oxazolyl) | CH₂CO₂H | CH₂ | 3,4-Cl₂-phe |
| 7-SO₂Me | 5-(2-oxazolyl) | CH₂CO₂H | CH₂ | 4-Cl-phe |
| 7-SO₂Me | 5-i-Pr | CH₂CO₂H | CH₂ | 2,4-Cl₂-phe |
| 7-SO₂Me | 5-i-Pr | CH₂CO₂H | CH₂ | 3,4-Cl₂-phe |
| 7-SO₂Me | 5-i-Pr | CH₂CO₂H | CH₂ | 4-Cl-phe |
| 7-SO₂Me | 5-c-Pr | CH₂CO₂H | CH₂ | 2,4-Cl₂-phe |
| 7-SO₂Me | 5-c-Pr | CH₂CO₂H | CH₂ | 3,4-Cl₂-phe |
| 7-SO₂Me | 5-c-Pr | CH₂CO₂H | CH₂ | 4-Cl-phe |
| 7-F | 5-i-Pr | CH₂CO₂H | CH₂ | 2,4-Cl₂-phe |
| 7-F | 5-i-Pr | CH₂CO₂H | CH₂ | 3,4-Cl₂-phe |
| 7-F | 5-i-Pr | CH₂CO₂H | CH₂ | 4-Cl-phe |
| 7-F | 5-c-Pr | CH₂CO₂H | CH₂ | 2,4-Cl₂-phe |
| 7-F | 5-c-Pr | CH₂CO₂H | CH₂ | 3,4-Cl₂-phe |
| 7-F | 5-c-Pr | CH₂CO₂H | CH₂ | 4-Cl-phe |
| 7-F | 5-i-Bu | CH₂CO₂H | CH₂ | 2,4-Cl₂-phe |
| 7-F | 5-i-Bu | CH₂CO₂H | CH₂ | 3,4-Cl₂-phe |
| 7-F | 5-i-Bu | CH₂CO₂H | CH₂ | 4-Cl-phe |
| 7-F | 5-Br | CH₂CO₂H | CH₂ | 2,4-Cl₂-phe |
| 7-F | 5-Br | CH₂CO₂H | CH₂ | 3,4-Cl₂-phe |
| 7-F | 5-Br | CH₂CO₂H | CH₂ | 4-Cl-phe |
| 7-F | 5-I | CH₂CO₂H | CH₂ | 2,4-Cl₂-phe |
| 7-F | 5-I | CH₂CO₂H | CH₂ | 3,4-Cl₂-phe |
| 7-F | 5-I | CH₂CO₂H | CH₂ | 4-Cl-phe |
| 6,8-Cl₂ | 7-F | CH₂CO₂H | CH₂ | 2,4-Cl₂-phe |
| 6,8-Cl₂ | 7-F | CH₂CO₂H | CH₂ | 3,4-Cl₂-phe |
| 6,8-Cl₂ | 7-F | CH₂CO₂H | CH₂ | 4-Cl-phe |
| 7-F | 5-c-Bu | CH₂CO₂H | CH₂ | 2,4-Cl₂-phe |
| 7-F | 5-c-Bu | CH₂CO₂H | CH₂ | 3,4-Cl₂-phe |
| 7-F | 5-c-Bu | CH₂CO₂H | CH₂ | 4-Cl-phe |
| 7-F | 5-C(OH)(CH₂)₃ | CH₂CO₂H | CH₂ | 2,4-Cl₂-phe |
| 7-F | 5-C(OH)(CH₂)₃ | CH₂CO₂H | CH₂ | 3,4-Cl₂-phe |
| 7-F | 5-C(OH)(CH₂)₃ | CH₂CO₂H | CH₂ | 4-Cl-phe |
| 7-SO₂Me | 5-C(OH)(CH₂)₃ | CH₂CO₂H | CH₂ | 2,4-Cl₂-phe |
| 7-SO₂Me | 5-C(OH)(CH₂)₃ | CH₂CO₂H | CH₂ | 3,4-Cl₂-phe |
| 7-SO₂Me | 5-C(OH)(CH₂)₃ | CH₂CO₂H | CH₂ | 4-Cl-phe |
| 7-SO₂Me | 5-(2-oxetanyl) | CH₂CO₂H | CH₂ | 2,4-Cl₂-phe |
| 7-SO₂Me | 5-(2-oxetanyl) | CH₂CO₂H | CH₂ | 3,4-Cl₂-phe |
| 7-SO₂Me | 5-(2-oxetanyl) | CH₂CO₂H | CH₂ | 4-Cl-phe |
| 7-F | 5-(2-oxetanyl) | CH₂CO₂H | CH₂ | 2,4-Cl₂-phe |
| 7-F | 5-(2-oxetanyl) | CH₂CO₂H | CH₂ | 3,4-Cl₂-phe |
| 7-F | 5-(2-oxetanyl) | CH₂CO₂H | CH₂ | 4-Cl-phe |

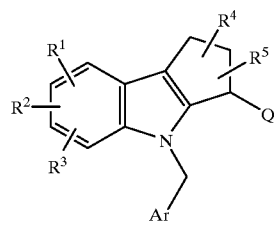

| $R^1/R^2$ | $R^3$ | $R^4/R^5$ | Q | Ar |
|---|---|---|---|---|
| 7-F | 5-CO₂Me | 1-OH | CH₂CO₂H | 2,4-Cl₂-phe |
| 7-F | 5-CO₂Me | 1-OH | CH₂CO₂H | 3,4-Cl₂-phe |
| 7-F | 5-CO₂Me | 1-OH | CH₂CO₂H | 4-Cl-phe |
| 7-F | 5-CO₂Me | 2-OH | CH₂CO₂H | 2,4-Cl₂-phe |
| 7-F | 5-CO₂Me | 2-OH | CH₂CO₂H | 3,4-Cl₂-phe |
| 7-F | 5-CO₂Me | 2-OH | CH₂CO₂H | 4-Cl-phe |

| | | -continued | | |
|---|---|---|---|---|
| 7-F | 5-CO$_2$Me | 1-oxo | CH$_2$CO$_2$H | 2,4-Cl$_2$-phe |
| 7-F | 5-CO$_2$Me | 1-oxo | CH$_2$CO$_2$H | 3,4-Cl$_2$-phe |
| 7-F | 5-CO$_2$Me | 1-oxo | CH$_2$CO$_2$H | 4-Cl-phe |
| 6,8-F$_2$ | 5-COMe | 2-OH | CH$_2$CO$_2$H | 2,4-Cl$_2$-phe |
| 6,8-F$_2$ | 5-COMe | 1-OH | CH$_2$CO$_2$H | 3,4-Cl$_2$-phe |
| 6,8-F$_2$ | 5-COMe | 1-oxo | CH$_2$CO$_2$H | 4-Cl-phe |

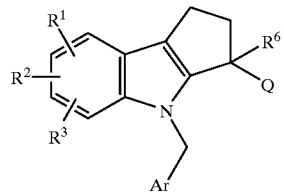

| R$^1$/R$^2$ | R$^3$ | Q and R$^6$ | Ar |
|---|---|---|---|
| 7-F | 5-C(O)CH$_3$ | cyclopropyl-CO$_2$H | 2,4-Cl$_2$-phe |
| 7-F | 5-C(O)CH$_3$ | " | 3,4-Cl$_2$-phe |
| 7-F | 5-C(O)CH$_3$ | " | 4-Cl-phe |
| 7-F | 5-CH(OH)CH$_3$ | cyclobutyl-CO$_2$H | 2,4-Cl$_2$-phe |
| 7-F | 5-CH(OH)CH$_3$ | " | 3,4-Cl$_2$-phe |
| 7-F | 5-CH(OH)CH$_3$ | " | 4-Cl-phe |
| 7-SO$_2$Me | 5-CO$_2$Me | cyclopropyl-CO$_2$H | 4-Cl-phe |
| 7-SO$_2$Me | 5-CO$_2$Me | cyclobutyl-CO$_2$H | 4-Cl-phe |
| 7-SO$_2$Me | 5-c-Pr | oxetanyl-CO$_2$H | 4-Cl-phe |
| 7-F | 5-CH(OH)CH$_3$ | oxetanyl-CO$_2$H | 3,4-Cl$_2$-phe |
| 6,8-Cl$_2$ | 7-SO$_2$Me | cyclopropyl-CO$_2$H | 4-Cl-phe |

Assays for Determining Biological Activity

Compounds of formula I can be tested using the following assays to determine their prostanoid antagonist or agonist activity in vitro and in vivo and their selectivity. The prostaglandin receptor activities demonstrated are DP, EP$_1$, EP$_2$, EP$_3$, EP$_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293(ebna) cells. HEK 293(ebna) cells expressing the individual cDNAs are grown under selection and individual colonies are isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 $\mu$M of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Prevention of PGD2 or Allergen Induced Nasal Congestion in Allergic Sheep

Animal preparation: Healthy adult sheeps (18–50 kg) are used. These animals are selected on the basis of a natural positive skin reaction to an intradermal injection of Ascaris suum extract.

Measurements of nasal congestion: The experiment is performed on conscious animals. They are restained in a cart in a prone position with their heads immobilized. Nasal airway resistance (NAR) is measured using a modified mask rhinometry technique. A topical anaesthesia (2% lidocaine) is applied to the nasal passage for the insertion of a nasotracheal tube. The maximal end of the tube is connected to a pneumotachograph and a flow and pressure signal is recorded on an oscilloscope linked to a computer for on-line calculation of NAR. Nasal provocation is performed by the administration of an aerosolized solution (10 puffs/nostril). Changes in the NAR congestion are recorded prior to and for 60–120 minutes post-challenge.

Prevention of PGD2 and Allergen Induced Nasal Obstruction in Cynomolgus Monkey

Animal preparation: Healthy adult male cynomologus monkeys (4–10 kg) are used. These animals are selected on the basis of a natural positive skin reaction to an intradermal injection of Ascaris suum extract. Before each experiment, the monkey selected for a study is fasted overnight with water provided at libitum. The next morning, the animal is sedated with ketamine (10–15 mg/kg i.m.) before being removed from its home cage. It is placed on a heated table (36° C.) and injected with a bolus dose (5–12 mg/kg i.v.) of propofol. The animal is intubated with a cuffed endotracheal tube (4–6 mm I.D.) and anaesthesia is maintained via a continuous intravenous infusion of propofol (25–30 mg/kg/ h). Vital signs (heart rate, blood pressure, respiratory rate, body temperature) are monitored throughout the experiment.

Measurements of nasal congestion: A measurement of the animal respiratory resistance is taken via a pneumotachograph connected to the endotracheal tube to ensure that it is normal. An Ecovision accoustic rhinometer is used to evaluate nasal congestion. This technique gives a non-invasive 2D echogram of the inside of the nose. The nasal volume and the minimal cross-sectional area along the length of the nasal cavity are computed within 10 seconds by a laptop computer equipped with a custom software (Hood Laboratories, Mass, U.S.A.). Nasal challenge is delivered directly to the animal's nasal cavity (50 $\mu$L volume). The changes in nasal congestion are recorded prior to and for 60–120 minutes post-challenge. If nasal congestion occurs, it will translate into a reduction in the nasal volume.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either PGD2 or Ascaris suum antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of mediator or Ascaris antigen response by the test compound. For statistical analysis, paired t-test is used. (References: MeFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.); and b) they have previously responded to inhalation challenge with Ascaris suum with both an acute bronchoconstriction and a late bronchial obstruction (W. M. Abraham et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

The invention will now be illustrated in the following non-limiting Examples in which, unless otherwise stated:

1. All the end products of the formula I were analyzed by NMR, TLC and elementary analysis or mass spectroscopy.
2. Intermediates were analyzed by NMR and TLC.
3. Most compounds were purified by flash chromatography on silica gel, recrystallization and/or swish (suspension in a solvent followed by filtration of the solid).
4. The course of reactions was followed by thin layer chromatography (TLC) and reaction times are given for illustration only.
5. The enantiomeric excess was measured on normal phase HPLC with a chiral column: ChiralPak AD; 250×4.6 mm.

The following intermediates were prepared according to literature procedures or purchased from the following vendor:

1. Ethyl 2-(2-oxocyclopentyl)acetate: Acros/Fisher Scientific.
2. 4-fluoro-2-iodoaniline: Beugelmans, R.; Chbani, M. *Bull. Soc. Chim. Fr.* 1995, 132, 306–313.
3. Ethyl 2-(1-methyl-2-oxocyclopentyl)acetate: Hudlicky, T., Short, R. P.; Revol, J.-M.; Ranu, B. C. *J. Org. Chem.* 1983, 48, 4453–4461.
4. 4-Methylsulfonylaniline hydrochloride: Acros/Fisher Scientific.

EXAMPLE 1

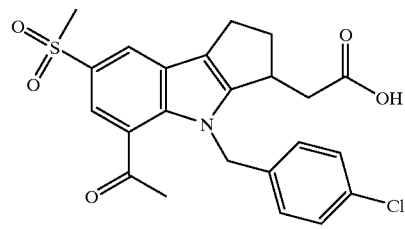

(+/−)-2-{5-Acetyl-4-[(4-chlorophenyl)methyl]-7-(methylsulfonyl)-1,2,3-trihydrocyclopenta[2,3-b]indol-3-yl}acetic Acid Step 1

2-Iodo-4-(methylsulfonyl)phenylamine

To a vigorously stilted solution of 100 g of 4-(methylsulfonyl)-phenylamine dissolved in 5.5 L of EtOH at 50° C. was added a mixture of 49.3 g of iodine and 110 g of silver sulfate in 1 L of EtOH. This was repeated after 1 h of stirring. After another hour, a mixture of 49.3 g of iodine and 43.8 g of silver sulfate in 1 L of EtOH was added and the mixture stirred overnight. The hot solution was then filtered through Celite and the solvent stripped. The residue was triturated with 1 L of EtOH at 50° C. for 45 min and cooled to 0° C. The product was filtered and collected to give 140 g of the title compound as a brown solid.

$^1$H NMR (acetone-$d_6$) δ7.95 (1H, d), 7.54 (1H, dd), 6.79 (1H, d), 6.19 (2H, br s), 3.08 (3H, s). MS (+APCI) m/z 298.2 (M+H)$^+$ Step 2

(+/−)-Ethyl 2-[7-(methylsulfonyl)-1,2,3-trihydrocyclopenta[2,3-b]indol-3-yl]-acetate

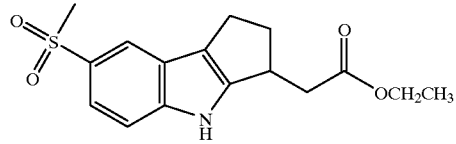

To a solution of 150 g of 2-iodo-4-(methylsulfonyl) phenylamine and 4.8 g of PTSA in 30 ml of DMF degassed and kept under a $N_2$ atmosphere, 135 g of tetraethoxysilane and 129 g of ethyl 2-(2-oxocyclopentyl)acetate were added successively. The final mixture was heated to 130–140° C. and stirred for 6 h. Then, 30 ml of DMF was added and the solution was degassed before 270 ml of Hunig's base followed by 3.4 g of Pd(OAc)$_2$ were added successively. The solution was heated to 120° C. for 2 h, then cooled to room temperature. To quench the reaction, 300 ml of 1 N HCl and 200 ml of isopropyl acetate were added and the mixture was filtered through Celite. The phases were separated and the acidic phase was extracted twice with 200 ml of isopropyl acetate. The organic layers were combined, washed with brine, dried over anhydrous $Na_2SO_4$, filtered through Celite and concentrated. The crude material was further purified by flash chromatography eluting with 50% EtOAc in hexanes to provide 63 g of the title compound as a yellow solid.

¹H NMR (acetone-d₆) δ10.23 (1H, br s), 7.98 (1H, s), 7.58 (2H, m), 4.14 (2H, q), 3.63 (1H, s), 3.04 (3H, s), 2.90–2.65 (5H, m), 2.19 (1H, m), 1.22 (3H, t). MS (+APCI) m/z 322.2 (M+H)⁺.

Step 3

(+/−)-2-[7-(Methylsulfonyl)-1,2,3-trihydrocyclopenta[2,3-b]indol-3-yl]acetic acid

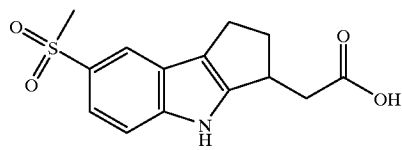

To a solution of 10.4 g of the ester of Step 2 in 80 mL of THF at room temperature, 40 mL of MeOH followed by 40 mL of 2N NaOH were added. After 1.5 h, the reaction mixture was poured into a separatory funnel containing EtOAc/1N HCl. The phases were separated and the acidic phase was extracted twice with EtOAc. The organic layers were combined, washed with brine, dried over anhydrous Na₂SO₄ and evaporated to dryness. The crude solid was swished in EtOAc/hexanes to give 9.1 g of the title acid as a faint brown solid.

¹H NMR (acetone-d₆) δ10.86 (1H, br s), 10.25 (1H, br s), 7.98 (1H, s), 7.58 (2H, m), 3.62 (1H, m), 3.04 (3H, s), 2.89–2.68 (5H, m), 2.21 (1H, m). MS (+APCI) m/z 294.0 (M+H)⁺

Step 4

(+/−)-2-[5-Bromo-7-(methylsulfonyl)-1,2,3-trihydrocyclopenta[2,3-b]indol-3-yl]acetic acid

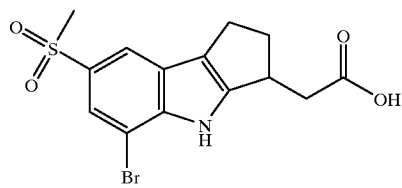

Pyridinium tribromide (154 g) was added to a solution of 2-[7-(methylsulfonyl)-1,2,3-trihydrocyclopenta[2,3-b]indol-3-yl]acetic acid (50.8 g) in pyridine at −25 to −30° C., the solution was warmed to 0° C. for 15 min and then to RT for 30 min. 1250 ml of 1:1 THF/ether and 2500 ml of 1:1 brine/6N HCl were added, the phases separated, the aqueous layer washed with 1:1 THF/ether and the combined organic layers were dried with Na₂SO₄. The organic phase was cooled to 10° C., acetic acid (50.5 ml) was added followed by a slow addition of zinc (70.2 g) (maintaining the temperature below 15° C.). The reaction mixture was stirred for 1 hour at RT. 3000 ml of 1N HCl and 1250 ml of EtOAc were added, the phases separated and the aqueous layer washed with 2000 ml EtOAc. The combined organic layers were dried with Na₂SO₄ and the solvent was stripped. The resulting brownish powder was swished with 1000 ml of 20% EtOAc/hexanes. 52 g (81%) of the title compound was isolated.

¹H NMR (acetone-d₆) δ10.38 (1H, br s), 8.00 (1H, d), 7.76 (1H, d), 3.66 (1H, m), 3.13 (3H, s), 3.00–2.75 (4H, m), 2.62 (1H, dd), 2.26 (1H, m). MS (−APCI) m/z 372.2, 370.2 (M−H)⁻

Step 5

(+/−)-Methyl 2-[5-bromo-7-(methylsulfonyl)-1,2,3-trihydrocyclopenta[2,3-b]indol-3-yl]acetate

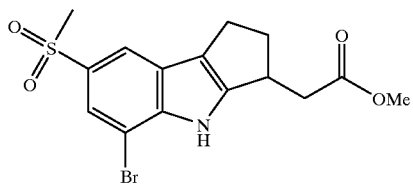

The acid of Step 4 was esterified in THF with an etheral solution of CH₂N₂. After removal of the solvents, the title ester was obtained quantitatively as a pale brown solid.

¹H NMR (acetone-d₆) δ10.41 (1H, br s), 8.00 (1H, d), 7.76 (1H, d), 3.68 (4H, m), 3.13 (3H, s), 3.00–2.75 (4H, m), 2.62 (1H, dd), 2.23 (1H, m).

Step 6

(+/−)-Methyl 2-{5-bromo-4-[(4-chlorophenyl)methyl]-7-(methylsulfonyl)-1,2,3-trihydrocyclopenta[2,3-b]indol-3-yl}acetate

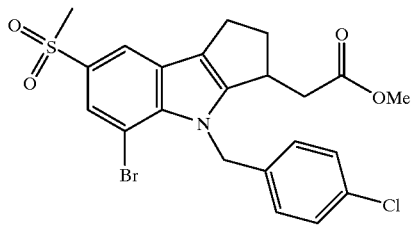

To a solution of 3.70 g of the indole of Step 5 in 30 mL of DMF at −78° C. was added 790 mg of a NaH suspension (60% in oil). The resulting suspension was stirred for 10 min at 0° C., cooled again to −78° C.? and treated with 2.36 g of 4-chlorobenzyl bromide. After 5 min, the temperature was warmed to 0° C. and stirred 20 min. At this time, the reaction mixture was quenched by the addition of 1 mL of AcOH and this mixture was poured into a separatoly funnel containing 1N HCl/EtOAc. The layers were separated and the organic layer was washed with brine, dried over anhydrous Na₂SO₄ and concentrated. The crude material was further purified by flash chromatography eluting with 10% EtOAc in toluene and swished in EtOAc/hexanes to yield 4.33 g of the title compound as a white solid.

¹H NMR (acetone-d₆) δ8.03 (1H, d), 7.74 (1H, d), 7.34 (2H, d), 6.95 (2H, d), 5.97 (1H, d), 5.86 (1H, d), 3.66 (1H, m), 3.57 (3H, s), 3.14 (3H, s), 2.99 (1H, m), 2.95–2.75 (2H, m), 2.67 (1H, dd), 2.45 (1H, dd), 2.28 (1H, m).

Step 7

(+/−)-Methyl 2-{5-acetyl-4-[(4-chlorophenyl)methyl]-7-(methylsulfonyl)-1,2,3-trihydrocyclopenta[2,3-b]indol-3-yl}acetate

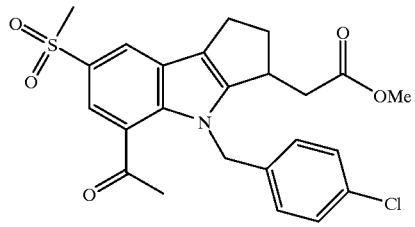

To a solution of 3.0 g of the bromoindole of Step 6 in 15 mL of DMF was added 3.97 mL of 1-ethoxyvinyl tributyltin. The resulting mixture was degassed by bubbling $N_2$ through the solution for several minutes. In a separate flask was placed 538 mg of $Pd_2(dba)_3$, 720 mg of $Ph_3As$ along with 9.0 mL of DMF and this mixture was sonicated for 1 min. The catalyst mixture was then introduced into the reaction flask and heated to 90° C. for 30 min. After allowing the reaction to cool to room temperature, 4 mL of a 1N HCl solution was added to the reaction flask and allowed to stir until TLC analysis indicated the consumption of the vinyl ether adduct. The reaction mixture was diluted with water, extracted with isopropyl acetate, dried over anhydrous $Na_2SO_4$ and concentrated. The resulting material was further purified by flash chromatography eluting with 20% acetone in toluene to provide 2.7 g of the title ketone as a white solid.

$^1$H NMR (CDCl$_3$) δ8.19 (1H, s), 7.74 (1H, s), 7.16 (2H, d), 6.55 (2H, d), 5.35 (1H, d), 5.29 (1H, d), 3.71 (1H, m), 3.65 (3H, s), 3.06 (3H, s), 3.05–2.80 (3H, m), 2.66 (1H, dd), 2.50 (1H, dd), 2.32 (1H, m), 2.12 (3H, s).

Step 8

(+/−)-2-{5-Acetyl-4-[(4-chlorophenyl)methyl]-7-(methylsulfonyl)-1,2,3-trihydrocyclopenta[2,3-b]indol-3-yl}acetic acid The title compound was prepared from 2.08 g of the ester of Step 7 according to procedure of Step 3, to yield 1.99 g of a brown solid.

$^1$H NMR (acetone-d$_6$) δ10.76 (1H, br s), 8.19 (1H, d), 7.87 (1H, d), 7.27 (2H, d), 6.73 (2H, d), 5.48 (2H, s), 3.79 (1H, m), 3.12 (3H, s), 3.05 (1H, m), 3.00–2.70 (3H, m), 2.55 (1H, dd), 2.38 (1H, m), 2.19 (3H, s).

$^{13}$CNMR (acetone-d$_6$) δ204.4, 177.3, 158.0, 142.5, 141.3, 137.5, 136.6, 133.6, 133.3, 132.3, 131.6, 126.6, 125.5, 124.5, 54.8, 48.9, 43.2, 40.5, 40.3, 33.1, 27.5.

MS (+APCI) m/z 460.5, 458.3 (M+H)$^+$.

EXAMPLE 2

(+)-2-{5-Acetyl-4-[(4-chlorophenyl)methyl]-7-(methylsulfonyl)-1,2,3-trihydrocyclopenta[2,3-b]Indol-3-yl}acetic Acid [(+)-isomer of Compound of Example 1]

150 to 200 mg of (+/−)-2-{5-acetyl-4-[(4-chlorophenyl)methyl]-7-(methylsulfonyl)-1,2,3-trihydrocyclopenta[2,3-b]indol-3-yl}acetic acid (example 1, step 8) dissolved in 10 mL of hot EtOH was resolved using normal phase preparative chiral HPLC [ChiralPak AD column: 50×5 cm, 20μ; mobile phase: hexane/2-propanol/acetic acid (70:30:0.4); flow: 70–75 mL/min; pressure: 280–300 PSI; U.V.: 265 nm]. Retention times of the two enantiomers were 38 min and 58 min. The title compound was obtain as the less polar enantiomer with 98% ee.

ee=98%; Retention time=12.1 min [ChiralPak AD column: 250×4.6 mm, hexane/2-propanol/acetic acid (75:25:0.1)].

Anal. Calcd for $C_{23}H_{22}ClNO_5S$: C, 60.06; H, 4.82; N, 3.05; S, 6.97. Found: C, 60.24; H, 4.55; N, 3.03; S, 7.20.

EXAMPLE 3

(−)-2-{5-Acetyl-4-[(4-chlorophenyl)methyl]-7-(methylsulfonyl)-1,2,3-trihydrocyclopenta[2,3-B]indol-3-yl}acetic Acid [(−)-isomer of Compound of Example 1]

150 to 200 mg of (+/−)-2-{5-acetyl-4-[(4-chlorophenyl)methyl]-7-(methylsulfonyl)-1,2,3-trihydrocyclopenta[2,3-b]indol-3-yl}acetic acid (example 1, step 8) dissolved in 10 ml of hot EtOH was resolved in normal phase preparative chiral HPLC [ChiralPak AD column: 50×5 cm, 20μ; mobile phase: hexane/2-propanol/acetic acid (70:30:0.4); flow: 70–75 mL/min; pressure: 280–300 PSI; U.V.: 265 nm]. Retention times of the two enantiomers were 38 min and 58 min. The title compound was obtain as the more polar enantiomer with 96.7% ee. This enantiomer was recrystallized with 80% 2-propanol/hexanes to increase the ee. ee=96.7%; Retention time=15.3 min [ChiralPak AD column: 250×4.6 mm, hexane/2-propanol/acetic acid (75:25:0.1)]; $[\alpha]_D^{21}$=−10.9° (c 0.45, MeOH). Anal. Calcd for $C_{23}H_{22}ClNO_5S$: C, 60.06; H, 4.82; N, 3.05; S, 6.97. Found: C, 59.96; H, 4.81; N, 3.01; S, 7.22. M.p. 219.5° C.

EXAMPLE 3A

Alternative Method for the Preparation of Compound of Example 3

A. Resolution of (+)-2-[5-Bromo-7-(methylsulfonyl)-1,2,3-trihydrocyclopenta[2,3-b]indol-3-yl]acetic acid A suspension of 300 mg of (+/−)-2-[5-bromo-7-(methylsulfonyl)-1,2,3-trihydrocyclopenta[2,3-b]indol-3-yl]acetic acid (example 1, step 4) and 138 mg of (R)-(+)-1-(naphthyl)ethylamine in 15 ml of 2-propanol and 5 ml of acetone was dissolved by heating to reflux. The solvents were then removed under reduced pressure and the residue was recrystallized in a 1:1 mixture of 2-propanol/acetone (7 ml). After filtration, the white solid salt obtained was suspended in 5 ml methanol and treated with 3N HCl until pH 1. The precipitate was filtered and air dried to yield 78 mg of the title enantiomer. Retention times of the two enantiomers were 6.5 min and 8.2 min [ChiralPak AD column, hexane/2-propanol/acetic acid (75:25:0.2)]. The title compound was obtain as the more polar enantiomer with 90% ee. This procedure was repeated to obtain the aove compound with a 99% ee.

ee=99%; Retention time=8.2 min [ChiralPak AD column: 250×4.6 mm, hexane/2-propanol/acetic acid (75:25:0.2)]; $[\alpha]_D^{21}$=+11.0° (c 0.5, MeOH).

B. The procedure described in Example 1, steps 5–8 was followed using the above (+) enantiomer instead of the racemate to provide the compound of Example 3.

EXAMPLE 4

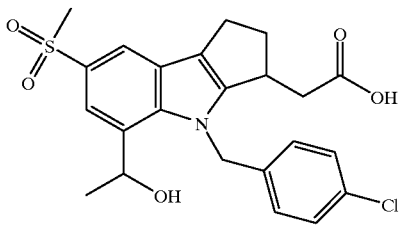

(+)-2-{4-[(4-Chlorophenyl)methyl]-5-(hydroxyethyl)-7-(methylsulfonyl)-1,2,3-trihydrocyclopenta[2,3-b]indol-3-yl}acetic Acid
(Deastereomer A)

Step 1. Reduction of Ketone

In a dry flask was placed 350 mg of (−)-2-{5-acetyl-4-[(4-chlorophenyl)methyl]-7-(methylsulfonyl)-1,2,3-trihydrocyclopenta[2,3-b]indol-3-yl}acetic acid (example 3; ee=99%) along with 30 ml of MeOH. To this stirred solution was added NaBH$_4$ portion-wise (ca. 50 mg/portion) in 10–15 min intervals until the consumption of ketone was noted by TLC analysis. At this time the reaction mixture was poured into a separatory funnel containing 100 mL of a saturated aqueous NH$_4$Cl solution/10 mL of a 1N HCl solution and 100 mL of EtOAc. The layers were separated and the aqueous layer was extracted with EtOAc, the combined organic layers were dried over anhydrous Na$_2$SO$_4$ and concentrated. The resulting material was purified by chiral HPLC as follows:

Step 2. Chiral Purification 150 to 200 mg of the previous mixture of alcohols dissolved in 10 mL of hot EtOH was resolved in normal phase preparative chiral HPLC [ChiralPak AD column: 50×5 cm, 20μ; mobile phase: hexane/2-propanol/acetic acid (80:20:0.4); flow: 70–75 mL/min; pressure: 280–300 PSI; U.V.: 245 nm]. Retention times of the two diastereoisomers were 33 min and 51 min. The title compound was obtain as the less polar diastereoisomer with >99% de.

ee=99%; de>99%; Retention time=6.0 min [ChiralPak AD column: 250×4.6 mm, hexane/2-propanol/acetic acid (75:25:0.2)]; [α]$_D^{21}$=+7.6° (c 1.0, MeOH).

$^1$H NMR (acetone-d$_6$) δ7.95 (1H, d), 7.83 (1H, d), 7.32 (2H, d), 6.90 (2H, d), 5.92 (1H, d), 5.65 (1H, d), 5.19 (1H, q), 3.60 (1H, m), 3.07 (3H, s), 2.99 (1H, m), 2.83 (2H, m), 2.65 (1H, dd), 2.39 (1H, m), 2.31 (1H, m), 1.45 (3H, d).

$^{13}$CNMR (acetone-d$_6$) δ173.3, 152.0, 141.1, 139.4, 133.3, 133.2, 132.6, 129.7, 127.8, 126.4, 121.7, 118.8, 117.3, 64.6, 50.3, 45.0, 39.1, 36.5, 36.2, 24.6, 23.5.

MS (−APCI) m/z 462.8, 460.5 (M−H)$^−$.

Anal. Calcd for C$_{23}$H$_{24}$ClNO$_5$S: C, 59.80; H, 5.24; N, 3.03; S, 6.94. Found: C, 59.47; H, 5.22; N, 2.96; S, 7.14. M.p. 212.4° C.

EXAMPLE 5

2-{4-[(4-Chlorophenyl)methyl]-5-(hydroxyethyl)-7-(methylsulfonyl)-1,2,3-trihydrocyclopenta[2,3-b]indol-3-yl}acetic Acid (Diastereomer B)

The material from Example 4, Step 1 (150 to 200 mg, ee=99%) dissolved in 10 mL of hot EtOH was resolved in normal phase preparative chiral HPLC [ChiralPak AD column: 50×5 cm, 20μ; mobile phase: hexane/2-propanol/acetic acid (80:20:0.4); flow: 70–75 mL/min; pressure: 280–300 PSI; U.V.: 245 nm]. Retention times of the two diastereoisomers were 33 min and 51 min. The title compound was obtain as the more polar diastereoisomer with >95% de.

ee=99%; de>95%; Retention time=7.9 min [ChiralPak AD Column: 250×4.6 mm, hexane/2-propanol/acetic acid (75:25:0.2)].

$^1$H NMR (acetone-d$_6$) δ7.95 (1H, d), 7.83 (1H, d), 7.32 (2H, d), 6.90 (2H, d), 6.00 (1H, d), 5.57 (1H, d), 5.20 (1H, q), 3.59 (1H, m), 3.07 (3H, s), 3.01 (1H, m), 2.82 (2H, m), 2.65 (1H, d), 2.45–2.25 (2H, m), 1.45 (3H, d). MS (−APCI) m/z 462.6, 460.5 (M−H)$^−$.

EXAMPLE 6

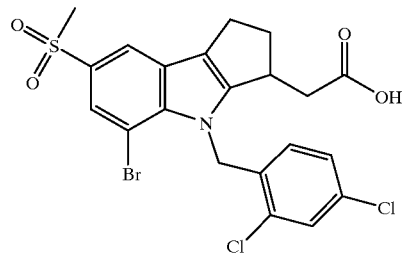

(+/−)-2-{4-[(2,4-Dichlorophenyl)methyl]-5-bromo-7-(methylsulfonyl)-1,2,3-trihydrocyclopenta[2,3-b]indol-3-yl}acetic Acid Following the coupling, procedure described in example 1, step 6, using 104 mg of methyl 2-[5-bromo-7-(methylsulfonyl)-1,2,3-trihydrocyclopenta[2,3-b]-indol-3-yl]acetate (example 1, step 5) and 50 μL of 2,4-dichlorobenzyl chloride gave 50 mg of the methyl ester of the title compound as a white solid (>95% purity).

$^1$H NMR (acetone-d$_6$) δ8.05 (1H, d), 7.73 (1H, d), 7.58 (1H, d), 7.24 (1H, dd), 6.28 (1H, d), 5.91 (1H, d), 5.85 (1H, d), 3.73 (1H, m), 3.55 (3H, s), 3.15 (3H, s), 3.01 (1H, m), 2.95–2.75 (2H, m), 2.68 (1H, dd), 2.49 (1H, dd), 2.30 (1H, m).

The title compound was prepared from 50 mg of the above methyl ester according to the procedure described in example 1, step 3, to yield 34 mg of a white solid (>95% purity).

$^1$H NMR (acetone-d$_6$) δ10.73 (1H, br s), 8.05 (1H, d), 7.73 (1H, d), 7.57 (1H, d), 7.23 (1H, dd), 6.28 (1H, d), 5.91 (2H, s), 3.71 (1H, m), 3.15 (3H, s), 3.02 (1H, m), 2.95–2.75 (2H, m), 2.68 (1H, dd), 2.47 (1H, dd), 2.34 (1H, m). MS (−APCI) m/z 532.3, 530.1, 527.9 (M−H)$^−$.

EXAMPLE 7

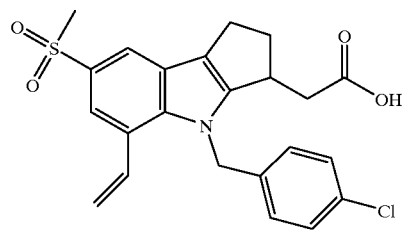

(+/−)-2-{4-[(4-Chlorophenyl)methyl]-7-(methylsulfonyl)-5-vinyl-1,2,3-trihydrocyclopenta[2,3-b]indol-3-yl}acetic Acid Using the method described in example 1, step 7, 112 mg of methyl 2-{5-bromo-4-[(4-chlorophenyl)methyl]-7-

(methylsulfonyl)-1,2,3-trihydrocyclopenta-[2,3-b]indol-3-yl}acetate (example 1, step 6) and 128 μL of vinyl tributyltin gave 94 mg of the methyl ester of the title compound as a yellow solid. This material was used without further purification in the next step.

The title compound was prepared from 17 mg of the above methyl ester according to the procedure described in example 1, step 3, to yield 16.5 mg of a colorless oil (>95% purity).

$^1$H NMR (acetone-$d_6$) δ10.68 (1H, br s), 7.98 (1H, s), 7.55 (1H, s), 7.35 (2H, d), 7.12 (1H, dd), 6.99 (2H, d), 5.74 (1H, d), 5.63 (1H, d), 5.66 (1H, d), 5.31 (1H, d), 3.64 (1H, m), 3.12 (3H, s), 3.10–2.75 (3H, m), 2.65 (1H, m), 2.50–2.25 (2H, m). MS (+APCI) m/z 463.0, 461.0 (M+NH$_4$)$^+$.

EXAMPLE 8

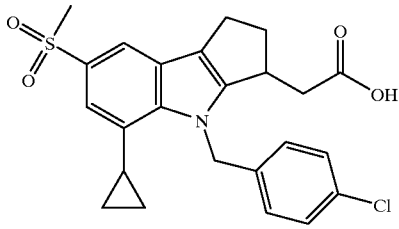

(+/−)-2-{4-[(4-Chlorophenyl)methyl]-5-cyclopropyl-7-(methylsulfonyl)-1,2,3-trihydrocyclopenta[2,3-b]indol-3-yl}acetic Acid To a round bottom flask containing 27.6 mg of the methyl 2-{4-[(4-chlorophenyl)methyl]-7-(methylsulfonyl)-5-vinyl-1,2,3-trihydrocyclopenta[2,3-b]-indol-3-yl}acetate (prepared in example 7) and 2 mL of THF cooled to 0° C. was added several mg of Pd(OAc)$_2$ and 4 mL of an etheral solution of CH$_2$N$_2$ and allowed to stir at this temperature. Additional portions of Pd(OAc)$_2$ and CH$_2$N$_2$ were added to the reaction mixture until $^1$H NMR analysis of an aliquot of the reaction mixture revealed the absence of vinylic hydrogens. The reaction mixture was filtered through a pad of silica gel and concentrated to furnish the methyl ester of the title compound.

$^1$H NMR (acetone-$d_6$) δ8.00 (1H, s), 7.34 (3H, m), 6.92 (2H, d), 6.04 (1H, d), 5.93 (1H, d), 3.54 (4H, m), 3.05 (3H, s), 2.96 (1H, m), 2.81 (2H, m), 2.65 (1H, dd), 2.43 (1H, dd), 2.25 (1H, m), 2.06 (1H, m), 0.95–0.70 (4H, m). MS (+APCI) m/z 495.8, 493.8 (M+Na)$^+$.

The title compound was prepared from 42 mg of the above methyl ester according to the procedure described in example 1, step 3, to yield 34 mg of a colorless oil.

$^1$H NMR (acetone-$d_6$) δ10.67 (1H, br s), 7.91 (1H, s), 7.33 (3H, m), 6.92 (2H, d), 6.06 (1H, d), 5.94 (1H, d), 3.58 (4H, m), 3.05 (3H, s), 2.99 (1H, m), 2.38 (2H, m), 2.64 (1H, dd), 2.50–2.25 (2H, m), 2.09 (1H, m), 1.00–0.70 (4H, m). MS (+APCI) m/z 477.2, 474.9 (M+NH$_4$)$^+$.

EXAMPLE 9

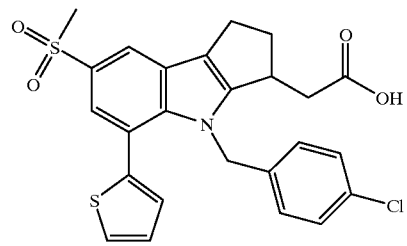

(+/−)-2-{4-[(4-Chlorophenyl)methyl]-7-(methylsulfonyl)-5-(2-thienyl)-1,2,3-trihydrocyclopenta[2,3-b]indol-3-yl}acetic Acid Using the method described in example 1, step 7, 500 mg of methyl 2-{5-bromo-4-[(4-chlorophenyl)methyl]-7-(methylsulfonyl)-1,2,3-trihydrocyclopenta-[2,3-b]indol-3-yl}acetate (example 1, step 6) and 600 μL of 2-thiophenyl tributyltin gave 480 mg of the methyl ester of the title compound as a faint yellow oil. This material was used without further purification in the next step.

$^1$H NMR (CDCl$_3$) δ8.09 (1H, s), 7.52 (1H, s), 7.28 (1H, d), 7.07 (2H, d), 6.91 (1H, m), 6.71 (1H, m), 6.35 (2H, d), 5.03 (1H, d), 4.96 (1H, d), 3.61 (3H, s), 3.49 (1H, m), 3.07 (3H, s), 3.05–2.70 (3H, m), 2.51 (1H, dd), 2.39 (1H, dd), 2.25 (1H, m).

The title compound was prepared from 480 mg of the above methyl ester according to the procedure described in example 1, step 3, to yield 450 mg of a white foam.

$^1$H NMR of the sodium salt (dmso-$d_6$) δ8.00 (1H, d), 7.59 (1H, dd), 7.31 (1H, d), 7.18 (2H, d), 7.04 (1H, dd), 6.94 (1H, m), 6.37 (2H, d), 5.26 (1H, d), 5.04 (1H, d), 3.42 (1H, m), 3.20 (3H, s), 2.88 (1H, m), 2.78 (1H, m), 2.62 (1H, m), 2.25–2.05 (2H, m), 1.92 (1H, dd). MS (−APCI) m/z 500.3, 498.2 (M−H)$^-$.

EXAMPLE 10

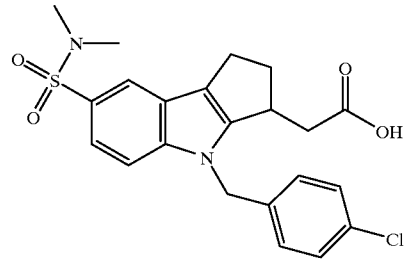

(+/−)-2-{7-[(Dimethylamino)sulfonyl]-4-[(4-chlorophenyl)-methyl]-1,2,3-trihydrocyclopenta[2,3-b]indol-3-yl}acetic Acid Step 1

[(4-Aminophenyl)sulfonyl]dimethylamine

To a solution of 40.2 g of sulfanilamide in 1.5 L of MeOH cooled at 0° C., 220 mL of dimethylsulfate and 464 mL of NaOH 5N were added simultanously via two syringe pumps over a period of 3 h. After consumption of the starting material, the organic solvent was removed under vacuum, aqueous NH$_4$Cl was added and the product was extracted with EtOAc. The organic layer was washed with water, brine and dried over anhydrous Na₂SO₄. The organic phase was concentrated to dryness and the crude solid was recrystallized from 90% EtOAc in hexanes to give 26.2 g of the title compound as a white solid.

¹H NMR (CDCl₃) δ7.53 (2H, d), 6.69 (2H, d) 4.12 (2H, br s), 2.64 (6H, s).

Step 2

[(4-Amino-3-iodophenyl)sulfonyl]dimethylamine

Using the method described in example 1, step 1, starting with 6.1 g of [(4-aminophenyl)sulfonyl]dimethylamine, 4.2 g of the title compound was obtained as a brown solid.

¹H NMR (CDCl₃) δ8.01 (1H, d), 7.51 (1H, dd), 6.75 (1H, d), 4.58 (2H, br s), 2.66 (6H, s).

Step 3

(+/−)-Ethyl 2-{7-[(dimethylamino)sulfonyl]-1,2,3-trihydrocyclopenta[2,3-b]-indol-3-yl}acetate

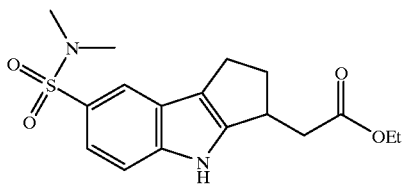

The title compound was prepared from 3.46 g of [(4-amino-3-iodo-phenyl)sulfonyl]dimethylamine and 1.91 g of ethyl 2-(2-oxocyclopentyl)acetate according to the procedure described in example 1, step 2, to yield 1.11 g of a white solid.

¹H NMR (acetone-d₆) δ10.23 (1H, br s), 7.84 (1H, d), 7.58 (1H, d), 7.44 (1H, dd) 4.15 (2H, q), 3.63 (1H, m), 2.95–2.65 (5H, m), 2.61 (6H, s), 2.21 (1H, m), 1.22 (3H, t). MS (−APCI) m/z 349.2 (M−H)⁻.

Step 4

(+/−)-2-{7-[(Dimethylamino)sulfonyl]-4-[(4-chlorophenyl)methyl]-1,2,3-trihydrocyclopenta[2,3-b]indol-3-yl}acetic acid Using the method described in example 1, step 6, 497 mg of the ester of Step 3 and 354 mg of 4-chlorobenzyl bromide gave the ethyl ester of the title compound, which was hydrolyzed according to example 1, step 3, to yield 500 mg of the title compound as a white solid.

¹H NMR (acetone-d₆) δ10.78 (1H, br s), 7.90 (1H, s), 7.46 (2H, m), 7.33 (2H, d), 7.12 (2H, d), 5.59 (1H, d), 5.49 (1H, d), 3.64 (1H, m), 2.97 (1H, m), 2.90–2.70 (3H, m), 2.61 (6H, s), 2.45 (1H, dd), 2.30 (1H, m). MS (−APCI) m/z 445.4 (M−H)⁻.

EXAMPLE 11

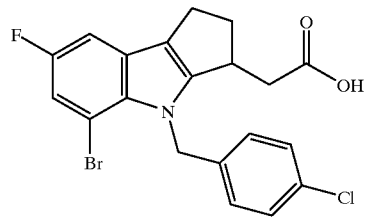

(+/−)-2-{5-Bromo-4-[(4-chlorophenyl)methyl]-7-fluoro-1,2,3-trihydrocyclopenta[2,3-b]indol-3-yl}acetic Acid Step 1

(+/−) 2-(7-fluoro-1,2,3-trihydrocyclopenta[2,3-b]indol-3-yl)acetic acid

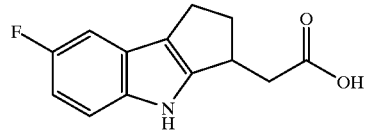

The ethyl ester of the title compound was prepared from 10.00 g of 4-fluoro-2-iodophenylamine and 6.57 g of ethyl 2-(2-oxocyclopentyl)acetate according to example 1, step 2, to yield 5.36 g of a yellow solid.

¹H NMR (acetone-d₆) δ9.76 (1H, br s), 7.34 (1H, dd), 7.03 (1H, d), 6.78 (1H, td), 4.14 (2H, q), 3.57 (1H, m), 2.85–2.55 (5H, m), 2.15 (1H, m), 1.22 (3H, t).

The title compound was prepared from 1.24 g of the above ethyl ester according to example 1, step 3, to yield 1.08 g of a crude and unstable waxy brown oil that was used such as in the next step (>90% purity).

¹H NMR (acetone-d₆) δ10.90 (1H, br s), 9.77 (1H, br s), 7.34 (1H, dd), 7.04 (1H, dd), 6.79 (1H, td), 3.56 (1H, m), 2.90–2.50 (5H, m), 2.16 (1H, m). MS (−APCI) m/z 232.2 (M−H)⁻.

Step 3

(+/−)-2-(5-Bromo-7-fluoro-1,2,3-trihydrocyclopenta[2,3-b]indol-3-yl)acetic acid

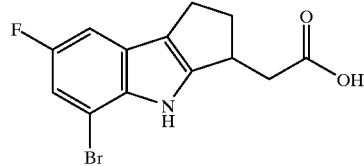

Using the method described in example 1, step 4, starting with 2.2 g of the acid of Step 2 (>90% purity), 2.13 g of the title compound was obtained as a crude and unstable brown solid. This material was used without further purification in the next step.

¹H NMR (acetone-d₆) δ10.77 (1H, br s), 9.84 (1H, br s), 7.09 (2H, m), 3.60 (1H, m), 2.95–2.65 (4H, m), 2.56 (1H, dd), 2.19 (1H, m).

Step 4

(+/−)-2-{5-Bromo-4-[(4-chlorophenyl)methyl]-7-fluoro-1,2,3-trihydrocyclopenta[2,3-b]indol-3-yl}acetic acid Esterification of 2.13 g of the previous acid with diazomethane followed by alkylation with 1.7 g of 4-chlorobenzyl bromide according to the methods described in example 1, steps 5 & 6, gave the methyl ester of the title compound, which was hydrolyzed using example 1, step 3. 2.35 g of the title compound was obtained as a brown solid.

$^1$H NMR (acetone-$d_6$) δ10.70 (1H, br s), 7.31 (2H, d), 7.18 (1H, d), 7.06 (1H, d) 6.92 (2H, d), 5.90 (1H, d), 5.74 (1H, d), 3.61 (1H, m), 3.00–2.70 (3H, m), 2.65 (1H, dd), 2.39 (1H, dd), 2.26 (1H, m). MS (–APCI) m/z 436.3, 434.5 (M–H)$^-$.

EXAMPLE 12

(+)-2-{5-Bromo-4-[(4-chlorophenyl)methyl]-7-fluoro-1,2,3-trihydrocyclopenta[2,3-b]indol-3-yl}acetic Acid [(+)-isomer of Compound of Example 11]

To a solution of 2.35 g of (+/–)-2-{5-bromo-4-[(4-chlorophenyl)-methyl]-7-fluoro-1,2,3-trihydrocyclopenta[2,3-b]indol-3-yl}acetic acid (example 11, step 4) in 130 mL of EtOH at 80° C., 780 μL of (S)-(–)-1-(naphthyl) ethylamine was added. The solution was cooled to room temperature and stirred overnight. 1.7 g of the salt recovered was recrystallized again with 200 mL of EtOH. After filtration, the white solid salt obtained was neutralized with 1N HCl and the product was extracted with EtOAc. The organic layer was washed with brine, dried over anhydrous $Na_2SO_4$ and concentrated. The material was filtered over a pad of $SiO_2$ by eluting with EtOAc to yield 500 mg of the title enantiomer as a white solid. Retention times of both enantiomers were respectively 7.5 min and 9.4 min [ChiralPak AD column, hexane/2-propanol/acetic acid (95:5:0.1)]. The more polar enantiomer was in 98% ee.

ee=98%; Retention time=9.4 min [ChiralPak AD column: 250×4.6 mm, hexane/2-propanol/acetic acid (75:25:0.1)]; $[\alpha]D^{21}$=+39.2° (c 1.0, MeOH).

EXAMPLE 13

(–)-2-{5-Bromo-4-[(4-chlorophenyl)methyl]-7-fluoro-1,2,3-trihydrocyclopenta[2,3-b]indol-3-yl}acetic Acid [(–)-isomer of Compound of Example 11]

To a solution of 1.58 g of (+/–)-2-{5-bromo-4-[(4-chlorophenyl)-methyl]-7-fluoro-1,2,3-trihydrocyclopenta[2,3-b]indol-3-ylacetic acid (recovered from the supernatants of the resolution of example 12) in 180 mL of EtOH at 80° C., 530 μL of (R)-(+)-1-(naphthyl) ethylamine was added. The solution was cooled to room temperature and stirred overnight. 1.07 g of the salt recovered was recrystallized again with 120 mL of EtOH. After filtration, the white solid salt obtained was neutralized with 1N HCl and the product was extracted with EtOAc. The organic layer was washed with brine, dried over anhydrous $Na_2SO_4$ and concentrated. The material was filtered over a pad of $SiO_2$ by eluting with EtOAc to yield 640 mg of the title enantiomer as a white solid. Retention times of the two enantiomers were 7.5 min and 9.4 min [ChiralPak AD column, hexane/2-propanol/acetic acid (95:5:0.1)]. The less polar enantiomer obtained with >99% ee.

ee>99%; Retention time=7.4 min [ChiralPak AD column: 250×4.6 mm, hexane/2-propanol/acetic acid (75:25:0. 1)].

EXAMPLE 14

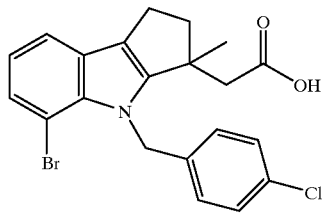

(+/–)-2-{5-Bromo-4-[(4-chlorophenyl)methyl]-3-methyl-1,2,3-trihydrocyclopenta[2,3-b]indol-3-yl}acetic Acid Step 1

(+/–)-Ethyl 2-(5-bromo-3-methyl-1,2,3-trihydrocyclopenta[2,3-b]indol-3-yl)-acetate

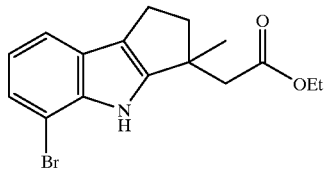

A suspension of 3.52 g of 2-bromophenylhydrazine and 2.90 g of ethyl 2-(1-methyl-2-oxocyclopentyl)acetate in 40 mL AcOH was heated at 100° C. for 1 hour. After this time, 20 mL of toluene was then added and the solvents were removed under reduced pressure. The crude material was purified by flash chromatography to afford 1.40g of the title compound as a yellow oil.

$^1$H NMR (acetone-$d_6$) δ9.85 (1H, br s), 7.38 (1H, d), 7.23 (1H, d), 6.93 (1H, t), 4.05 (2H, m), 2.80–2.60 (5H, m), 2.36 (1H, m), 1.40 (3H, s), 1.11 (3H, t). MS (–APCI) m/z 336.3 (M–H)$^-$.

Step 2

(+/–) 2-{5-bromo-4-[(4-chlorophenyl)methyl]-3-methyl-1,2,3-trihydrocyclopenta[2,3-b]indol-3-yl}acetic acid

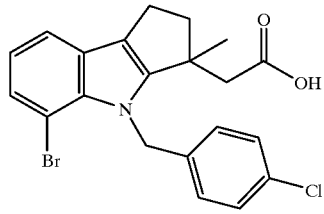

Using the method described in example 1, step 6, 390 mg of the previous ester from Step 1 and 222 mg of 4-chlorobenzyl chloride yielded 120 mg of the ethyl ester of the title compound as an off-white solid.

$^1$H NMR (acetone-$d_6$) δ7.44 (1H, d), 7.30 (2H, d), 7.22 (1H, d), 6.92 (1H, t), 6.90 (2H, d), 6.05 (1H, d), 5.85 (1H, d), 3.90 (2H, q), 2.80 (3H, m), 2.65 (2H, d), 2.36 (1H, m), 1.35 (3H, s), 1.00 (3H, t). MS (–APCI) m/z 458.3 (M–H)$^-$ The title compound was prepared from 105 mg of the above ethyl ester of the title compound according to example 1, step 3, to yield 90 mg of a white solid.

$^1$H NMR (acetone-$d_6$) δ10.50 (1H, br s), 7.43 (1H, d), 7.30 (2H, d), 7.22 (1H, d), 6.94 (1H, t), 6.90 (2H, d), 6.05 (1H, d), 5.80 (1H, d), 2.80 (3H, m), 2.65 (2H, d), 2.36 (1H, m), 1.35 (3H, s). MS (−APCI) m/z 432.2 (M+H)$^-$

What is claimed is:

1. A compound of formula I:

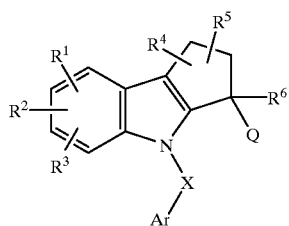

and pharmaceutically acceptable salts, hydrates and esters thereof, wherein:

$R^1$, $R^2$ and $R^3$ are each independently selected from the group consisting of:
(1) hydrogen, and
(2) $R^c$, $R^4$ and $R^5$ are each independently selected from the group consisting of:
(1) H,
(2) F,
(3) CN,
(4) $C_{1-6}$alkyl,
(5) $OR^a$, and
(6) $S(O)_nC_{1-6}$alkyl,
wherein each of said alkyl group is optionally substituted with halogen, or $R^4$ and $R^5$ on the same carbon atom may represent an oxo, or $R^4$ and $R^5$ on the same carbon atom or on adjacent carbon atoms taken together form a 3- or 4-membered ring containing 0 or 1 heteroatom selected from N, S, or O optionally substituted with one or two groups selected from F, $CF_3$ and $CH_3$;

$R^6$ is selected from the group consisting of:
(1) H,
(2) $C_{1-6}$alkyl optionally substituted with one to six groups independently selected from $OR^a$ and halogen, and
(3) heterocyclyl optionally substituted with one to four halogen; or $R^5$ and $R^6$ attached on adjacent carbon atoms together form a 3- or 4-membered ring containing 0 or 1 heteroatom selected from N, S, or O optionally substituted with one or two groups selected from F, $CF_3$ and $CH_3$;

X is selected from the group consisting of: C=O, $SO_2$, and $C_{1-4}$alkyl wherein said alkyl is optionally substituted with one to six halogen;

Ar is phenyl each optionally substituted with one to four groups independently selected from $R^c$;

Q is $C_{1-6}$alkyl substituted with COOH or tetrazolyl, or

Q and $R^6$ together form a 3- or 4-membered ring optionally containing a heteroatom selected from N, S, and O, and optionally substituted with one or two groups independently selected from:
(1) halogen,
(2) oxo,
(3) $OR^a$,
(4) COOH,
(5) $C(O)NHSO_2R^7$, and
(6) tetrazolyl, $R^7$ is selected from the group consisting of:
(1) $C_{1-6}$alkyl optionally substituted with one to six halogen,
(2) aryl, and
(3) heteroaryl,
wherein said aryl and heteroaryl are optionally substituted with halogen, $OC_{1-5}$alkyl, $C_{1-5}$alkyl and wherein said alkyl is optionally substituted with one to six halogen;

$R^a$ and $R^b$ are independently selected from hydrogen and $C_{1-6}$alkyl optionally substituted with one to six halogen;

$R^c$ is
(1) halogen,
(2) CN,
(3) $C_{1-6}$alkyl optionally substituted with one to six groups independently selected from halogen, $NR^aR^b$, $C(O)R^a$, $C(OR^a)R^aR^b$, and $OR^a$,
(4) $C_{2-6}$alkenyl optionally substituted with one to six groups independently selected from halogen and $OR^a$,
(5) heterocyclyl,
(6) aryl,
(7) heteroaryl,
(8) $C(O)R^a$,
(9) $C(OR^a)R^aR^b$,
(10) $C(O)OR^a$,
(11) $CONR^aR^b$,
(12) $OCONR^aR^b$,
(13) $S(O)_nR^7$,
(14) $NR^aC(O)OC_{1-6}$alkyl, wherein alkyl is optionally substituted with one to six halogen and
(15) $S(O)_nNR^aR^b$,
wherein heterocyclyl, aryl, heteroaryl are optionally substituted with one to four groups independently selected from halogen;

n is 1, 1 or 2.

2. A compound of claim 1 wherein X is $CH_2$.

3. A compound of claim 1 wherein Q is $C_{1-3}$alkyl substituted with COOH.

4. A compound of claim 1 wherein Q and $R^6$ together form a 3- or 4-membered ring containing 0 or 1 heteroatom selected from N, S and O, and optionally substituted with one or two groups selected from halogen, OH, COOH, oxo, tetrazolyl, $C(O)NHSO_2R^7$, $OC_{1-6}$alkyl wherein said alkyl group is optionally substituted with one to six halogen.

5. A compound of claim 1 wherein $R^3$ is H, $R^1$ and $R^2$ are selected from the group consisting of hydrogen, halogen, $C_{1-3}$alklyl (optionally substituted with one to six groups independently selected from halogen, $C(O)R^a$, and $C(OR^a)R^aR^b$), aryl, hetcroaryl, heterocyclyl, $C(O)OC_{1-3}$alkyl, $S(O)_nC_{1-3}$alkyl, $S(O)_nNR^aR^b$, $C(O)R^a$, $C(OH)R^aR^b$, and $C(OC_{1-3}$alkyl)$R^aR^b$, wherein each of aryl, heteroaryl, heterocyclyl, and alkyl is optionally substituted with one to six halogen atoms; n=0, 1 or 2; $R^a$ and $R^b$ are independently selected from hydrogen and $C_{1-6}$alkyl optionally substituted with halogen.

6. A compound of claim 1 wherein $R^4$ and $R^5$ are each independently selected from the group consisting of H, $C_{1-4}$alkyl optionally substituted with one to six halogen atoms and $OR^a$ wherein $R^a$ is as defined in claim 1; or $R^4$ and $R^5$ attached to the same carbon atom represent an oxo.

7. A compound of claim 1 wherein Ar is phenyl optionally substituted with one to four groups independently selected from halogen, CN, $C_{1-4}$alkyl optionally substituted with one to six halogen atoms, $C(O)R^a$ and $C(OH)R^aR^b$ wherein $R^a$ and $R^b$ are independently selected from hydrogen and $C_{1-6}$alkyl optionally substituted with halogen.

8. A compound of claim 1 having the formula Ia:

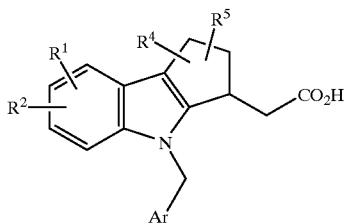

where Ar and $R^1$–$R^4$ are as defined in claim 1.

9. A compound of claim 8 wherein $R^4$ and $R^5$ are each hydrogen, and $R^1$ represents a non-H substituent at the 7-position.

10. A pharmaceutical composition comprising a compound of formula 1 and a pharmaceutically acceptable carrier.

11. A method for the treatment of prostaglandin mediated diseases which comprises administering to a patient in need of such treatment a therapeutically effective amount of a compound of claim 1.

12. A method for the treatment of prostaglandin D2 mediated diseases which comprises administering to a patient in need of such treatment a therapeutically effective amount of a compound of claim 1.

13. A method for the treatment of nasal congestion which comprises administering to a patient in need of such treatment a therapeutically effective amount of a compound of claim 1.

14. A method for the treatment of allergic asthma which comprises administering to a patient in need of such treatment a therapeutically effective amount of a compound of claim 1.

15. A method for the treatment of allergic rhinitis which comprises administering to a patient in need of such treatment a therapeutically effective amount of a compound of claim 1.

* * * * *

UNITED STATES PATENT AND TRADEMARK OFFICE
CERTIFICATE OF CORRECTION

PATENT NO. : 6,410,583 B1
DATED : June 25, 2002
INVENTOR(S) : Marc Labelle et al.

It is certified that error appears in the above-identified patent and that said Letters Patent is hereby corrected as shown below:

Column 42,
Line 40, should read: -- n is 0, 1 or 2. --.
Line 54, should read: -- $R^aR^b$), aryl, heteroaryl, heterocyclyl, $C(O)OC_{1-3}$alkyl, S(O) --.

Column 44,
Line 23, the following 3 Claims were missing from the issued Patent. They should read as follows:

-- 16. A compound of Claim 1 wherein X is $C_{1-4}$alkyl.

17. A compound of Claim 8 wherein Ar is phenyl optionally substituted with one to four groups independently selected from halogen, CN, $C_{1-4}$alkyl optionally substituted with one to six halogen atoms, $C(O)R^a$ and $C(OH)R^aR^b$ wherein $R^a$ and $R^b$ are independently selected from hydrogen and $C_{1-6}$alkyl optionally substituted with halogen.

UNITED STATES PATENT AND TRADEMARK OFFICE
CERTIFICATE OF CORRECTION

PATENT NO. : 6,410,583 B1
DATED : June 25, 2002
INVENTOR(S) : Marc Labelle et al.

It is certified that error appears in the above-identified patent and that said Letters Patent is hereby corrected as shown below:

18. A compound selected from:

2-{5-acetyl-4-[(4-chlorophenyl)methyl]-7-(methylsulfonyl)-1,2,3-trihydrocyclopenta[2,3-b]indol-3-yl]acetic acid;
  2-{4-[(4-chlorophenyl)methyl]-5-(hydroxyethyl)-7-(methylsulfonyl)-1,2,3-trihydrocyclopenta[2,3-b]indol-3-yl}acetic acid;
  2-{4-[(2,4-dichlorophenyl)methyl]-5-bromo-7-(methylsulfonyl)-1,2,3-trihydrocyclopenta[2,3-b]indol-3-yl}acetic acid;
  2-{4-[(4-chlorophenyl)methyl]-7-(methylsulfonyl)-5-vinyl-1,2,3-trihydrocyclopenta[2,3-b]indol-3-yl}acetic acid;
  2-{4-[(4-chlorophenyl)methyl]-5-cyclopropyl-7-(methylsulfonyl)1,2,3-trihydrocyclopenta[2,3-b]indol-3-yl}acetic acid;
  2-{4-[(4-chlorophenyl)methyl]-7-(methylsulfonyl)-5-(2-thienyl)1,2,3-trihydrocyclopenta[2,3-b]indol-3-yl}acetic acid;
  2-{7-[(dimethylamino)sulfonyl]-4-[(4-chlorophenyl)methyl]-1,2,3 trihydrocyclopenta[2,3-b]indol-3-yl}acetic acid;
  2-{5-bromo-4-[(4-chlorophenyl)methyl]-7-fluoro-1,2,3-trihydrocyclopenta[2,3-b]indol-3-yl}acetic acid;
  2-{5-bromo-4-[(4-chlorophenyl)methyl]-7-fluoro-1,2,3-trihydrocyclopenta[2,3-b]indol-3-yl}acetic acid;
  2-{5-bromo-4-[(4-chlorophenyl)methyl]-3-methyl-1,2,3-trihydrocyclopenta[2,3-b]-indol-3-yl}acetic acid. --.

Signed and Sealed this

Twenty-eighth Day of January, 2003

JAMES E. ROGAN
*Director of the United States Patent and Trademark Office*